United States Patent
Watanabe et al.

(10) Patent No.: US 11,661,390 B2
(45) Date of Patent: May 30, 2023

(54) ACETAL COMPOUNDS AND PROCESSES FOR PREPARING THEREOF, AND PROCESSES FOR PREPARING ALDEHYDE COMPOUNDS FROM THE ACETAL COMPOUNDS

(71) Applicant: Shin-Etsu Chemical Co., Ltd., Tokyo (JP)

(72) Inventors: Takeru Watanabe, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/861,629

(22) Filed: Jul. 11, 2022

(65) Prior Publication Data

US 2023/0062627 A1    Mar. 2, 2023

(30) Foreign Application Priority Data

Jul. 13, 2021  (JP) .............................. JP2021-115868

(51) Int. Cl.
 C07C 45/51     (2006.01)
 C07C 41/48     (2006.01)
 C07C 43/305    (2006.01)

(52) U.S. Cl.
 CPC ............ *C07C 45/513* (2013.01); *C07C 41/48* (2013.01); *C07C 43/305* (2013.01)

(58) Field of Classification Search
 CPC ...... C07C 45/513; C07C 41/48; C07C 43/305
 See application file for complete search history.

(56) References Cited

U.S. PATENT DOCUMENTS

2017/0342013 A1    11/2017  Wakamori et al.

FOREIGN PATENT DOCUMENTS

JP           2017210469 A     11/2017

OTHER PUBLICATIONS

Conia et al. "On the preparation of cyclopentenones by the action of polyphosphoric acid on esters of -ethylenic acids. Part 1: Practical aspects" Bulletin de la Societe Chimique de France, No. 8-9, pp. 2981-2991 (1970) (English machine translation).

Hajare et al. "Enantiospecific synthesis of sex pheromone of the obscure mealybug from pantolactone via tandem conjugate addition/cyclization" Tetrahedron Letters, 51:5291-5293 (2010).

Millar et al. "(2,3,4,4-Tetramethylcyclopentyl)methyl acetate, a sex pheromone from the obscure mealybug: first example of a new structural class of monoterpenes" Journal of Chemical Ecology, 31(12):2999-3005 (2005).

Millar et al. "Stereoselective synthesis of the obscure mealybug pheromone by hydrogenation of a tetrasubstituted alkene precursor" Tetrahedron Letters, 52:4224-4226 (2011).

Millar et al. "Synthesis of the sex pheromone of the obscure mealybug, the first example of a new class of monoterpenoids" Tetrahedron Letters, 48:6377-6379 (2007).

Morel-Fourrier et al. "Acylation of Alkenes Generated in Situ by Hydride Transfer from Isoalkanes. Synthesis of Pentalenones, Hydrindenones, and Cyclopentenones" Journal of the American Chemical Society, 113(21):8062-8069 (1991).

Extended European Search Report corresponding to European Patent Application No. 22183979.8 (5 pages) (dated Nov. 29, 2022).

Thomas et al. "Synthesis and stereochemistry of hydrogenated 1,1,4,4,7a-pentamethylindenes" Canadian Journal of Chemistry, 58(17):1810-1820 (1980).

*Primary Examiner* — Sikarl A Witherspoon
(74) *Attorney, Agent, or Firm* — Myers Bigel, P.A.

(57) ABSTRACT

The present invention relates to an acetal compound of the following general formula (1) and an acetal compound of the following general formula (2). The present invention relates to processes for preparing the acetal compound (2), comprising subjecting the acetal compound (1) to a hydrogenation reaction to form the acetal compound (2). The present invention provides a process for preparing 2,3,4,4-tetramethylcyclopentanecarbaldehyde of the following formula (3), comprising subjecting the acetal compound (2) to a hydrolysis reaction to form 2,3,4,4-tetramethylcyclopentanecarbaldehyde (3).

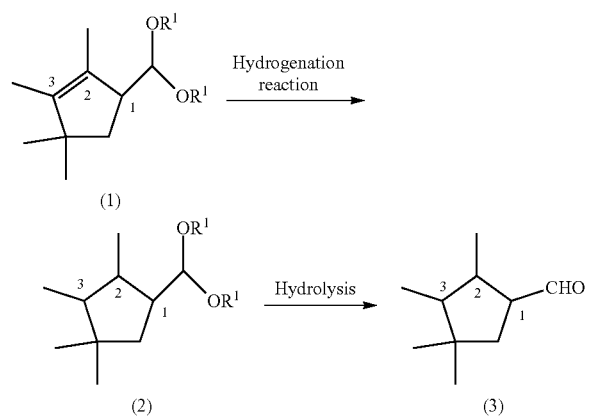

14 Claims, No Drawings

US 11,661,390 B2

ACETAL COMPOUNDS AND PROCESSES FOR PREPARING THEREOF, AND PROCESSES FOR PREPARING ALDEHYDE COMPOUNDS FROM THE ACETAL COMPOUNDS

TECHNICAL FIELD

The present invention relates to two novel acetal compounds and processes for preparing thereof. The present invention also relates to processes of preparing aldehyde compounds from the aforesaid acetal compounds, i.e., 2,3,4,4-tetramethylcyclopentanecarbaldehyde.

BACKGROUND ART

Insect sex pheromones are biologically active substances which are usually borne by females to attract males, and exhibit a high attracting activity at small amounts. Sex pheromones are widely utilized as a means for forecasting outbreaks of pests and/or confirming their geographic spread (invasion into a specific area), and also as a means for controlling pests. Widely used methods for controlling pests include a mass trapping method, a lure-and-kill or attract-and-kill method, a lure-and-infect or attract-and-infect method, and a mating disruption method. A naturally occurring sex pheromone can be extracted only in a trace amount from one insect. Therefore, it is difficult to use a naturally occurring sex pheromone for a mating disruption method. Before practical use of a sex pheromone, it is required to artificially produce a sufficient amount of the sex pheromone for basic research and also for applications.

*Pseudococcus viburni* (generic name: Obsucure Mealybug, hereinafter abbreviated as "OMB") which has spread mainly in the American continent, damages various crops including grapes and, therefore, is an economically serious insect. Recently, OMB has been increasingly spreading, and monitoring its geographic spread is important. The sex pheromone of OMB is reported to be (2,3,4,4-tetramethylcyclopentyl)methyl acetate which is one of (2,3,4,4-tetramethylcyclopentyl)methyl carboxylate compounds (Non-Patent Literature 1 listed below). It is also reported that in an attraction test for males with a synthetic racemic mixture of (1R*,2R*,3S*)-(2,3,4,4-tetramethylcyclopentyl)methyl acetate, the synthetic product exhibits an attracting activity comparable to that of the naturally occurring pheromone (Non-Patent Literature 1).

The sex pheromone of OMB is synthesized, for example, by subjecting a starting material isobutyl methacrylate to a Nazarov cyclization reaction (Non-Patent Literature 1 listed below). Improvements over the method described in Non-Patent Literature 1 are reported (Non-Patent Literatures 2 and 3 listed below). Specifically, methylenation of a ketone with dibromomethane, zinc, and titanium (IV) chloride is carried out to improve a yield. Both of these two Non-Patent Literatures use 2,3,4,4-tetramethylcyclopentanecarbaldehyde as a synthetic intermediate, specifically, it has been shown that (1R*,2R*,3S*)-(2,3,4,4-tetramethylcyclopentyl)methyl acetate having the relative configuration same as that of the naturally occurring sex pheromone of OMB may be easily synthesized from (1R*,2R*,3S*)-2,3,4,4-tetramethylcyclopentanecarbaldehyde among the four diastereomers of 2,3,4,4-tetramethylcyclopentanecarbaldehyde. Another process for synthesizing the optically active substance is also reported, in which (−)-pantolactone is used as a starting material, and a tandem conjugate addition/cyclization reaction is carried out as a key step (Non-Patent Literature 4 listed below). Also, a process intended to industrially produce the sex pheromone is disclosed by Wakamori et al., in which a Favorskii rearrangement reaction of α-halotetramethyl cyclohexanone is utilized (Patent Literature 1 listed below).

LIST OF THE LITERATURES

Patent Literature

[Patent Literature 1] Japanese Patent Application Laid-Open No. 2017-210469
[Non-Patent Literatures]
[Non-Patent Literature 1] J. Millar et al., J. Chem. Ecol., 31, 2999 (2005)
[Non-Patent Literature 2] J. Millar et al., Tetrahedron Lett., 48, 6377 (2007)
[Non-Patent Literature 3] J. Millar et al., Tetrahedron Lett., 52, 4224 (2011)
[Non-Patent Literature 4] D. Reddy et al., Tetrahedron Lett., 51, 5291 (2010)
[Non-Patent Literature 5] Bull. Soc. Chem. Fr., 2981 (1970)
[Non-Patent Literature 6] J. Am. Chem. Soc., 113, 8062 (1991)

Problems to be Solved by the Invention

The preparation process described in Non-Patent Literature 1 comprises less steps, but uses preparative gas chromatography to purify the target compound (2,3,4,4-tetramethylcyclopentyl)methyl acetate, and, therefore, the preparation of a large amount of (2,3,4,4-tetramethylcyclopentyl)methyl acetate in this synthesis process is difficult. The preparation processes described in Non-Patent Literatures 2 and 3 require mutagenic dibromomethane and an oxidation reaction with highly toxic hexavalent chromium, as well as silica gel column chromatography, which is costly and is difficult to scale up, for the purification of intermediates. This makes the synthesis processes difficult to carry out in an industrial scale. The preparation process described in Non-Patent Literature 4 requires so many steps as 17 to synthesize the target compound (2,3,4,4-tetramethylcyclopentyl)methyl acetate from (−)-pantolactone, comprises a conjugate addition reaction at an ultralow temperature of −78° C., and uses an explosive high-valent iodine reagent in an oxidation reaction. This makes the synthesis process difficult to carry out in an industrial scale.

On the other hand, although the process described in Patent Literature 1 is more industrially practical, there is demand for a more regioselective preparation process than the Favorskii rearrangement reaction.

Thus, it is difficult to industrially prepare a sufficient amount of (2,3,4,4-tetramethylcyclopentyl)methyl acetate in the known preparation processes, because of the use of the harmful reactants, the number of steps, the means for separation or purification of intermediates and/or the target compound, and other reasons. The known preparation processes also have room for improvement in the reaction selectivity.

SUMMARY OF THE INVENTION

The present invention has been made in these circumstances and aims to provide a process for preparing 2,3,4,4-tetramethylcyclopentanecarbaldehyde which is an important intermediate for the preparation of an OMB sex pheromone, i.e., (2,3,4,4-tetramethylcyclopentyl)methyl acetate, without any harmful reactants in less steps and with industrially feasible means for purification.

The present invention also aims to preferably provide a process for stereoselectively preparing a (1R*,2R*,3S*)-2,3,4,4-tetramethylcyclopentanecarbaldehyde having the relative configuration same as that of the naturally occurring sex pheromone of OMB, among four diastereomers of 2,3,4,4-tetramethylcyclopentanecarbaldehyde, and which may easily be converted into that racemic mixture in a diastereomeric ratio, dr, of 50% or more. The diastereomeric ratio, dr, refers to the number of moles of one diastereomer of interest divided by the total number of moles of all diastereomers present and multiplied by 100, expressed in %.

As a result of the intensive researches, the present inventors have found that the aforesaid two novel acetal compounds are useful intermediates for the preparation of 2,3,4,4-tetramethylcyclopentanecarbaldehyde.

As a result of the intensive researches, the present inventors have further found that a pathway via these two intermediates can be used to industrially prepare 2,3,4,4-tetramethylcyclopentanecarbaldehyde without any harmful reactants in less steps.

As a result of the intensive researches, the present inventors have further found that among the four diastereomers of 2,3,4,4-tetramethylcyclopentanecarbaldehyde, (1R*,2R*,3S*)-2,3,4,4-tetramethylcyclopentanecarbaldehyde having the relative configuration same as that of the naturally occurring sex pheromone of OMB may be prepared and may easily be converted into its racemic mixture in a diastereomeric ratio, dr, of 50% or more.

One aspect of the present invention provides a process for preparing an acetal compound of the following general formula (2), the process comprising:

subjecting an acetal compound of the following general formula (1) to a hydrogenation reaction to form the acetal compound (2):

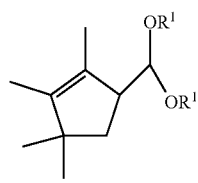

(1)

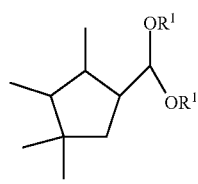

(2)

wherein in the general formulae (1) and (2), R¹s represent, independent of each other, a monovalent hydrocarbon group having 1 to 6 carbon atoms or two R¹s may form together a divalent hydrocarbon group, R¹—R¹, having 2 to 12 carbon atoms.

Another aspect of the present invention provides a process for preparing 2,3,4,4-tetramethylcyclopentanecarbaldehyde of the following formula (3):

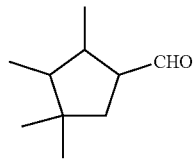

(3)

the process comprising:
the aforesaid process for preparing the acetal compound (2), and
subjecting the acetal compound (2) to a hydrolysis reaction to form 2,3,4,4-tetramethylcyclopentanecarbaldehyde (3).

Another aspect of the present invention provides the aforesaid process for preparing 2,3,4,4-tetramethylcyclopentanecarbaldehyde (3), wherein among four diastereomers of 2,3,4,4-tetramethylcyclopentanecarbaldehyde (3), the diastereomeric ratio, dr, of the (1R*,2R*,3S*)-2,3,4,4-tetramethylcyclopentanecarbaldehyde of the following formula (3") is 50% or more

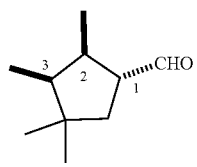

(3")

wherein in the formula (3"), the bold bond and the hashed bond represent a relative configuration.

Another aspect of the present invention provides the aforesaid process for preparing 2,3,4,4-tetramethylcyclopentanecarbaldehyde (3), the process further comprising:
subjecting a vinylether compound of the following general formula (4) and an alcohol compound of the following formulae (XA) or (XB) to an acetalization reaction in the presence of an acid to form the acetal compound (1)

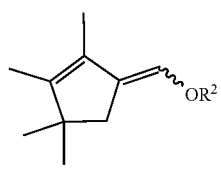

(4)

wherein in the general formula (4), R² represents a monovalent hydrocarbon group having 1 to 15 carbon atoms, and the wavy line represents the E-form, the Z-form, or a mixture thereof;
R¹OH (XA), wherein R¹ is as defined above; and
HOR¹—R¹OH (XB), wherein les represent, independent of each other, as defined above.

Another aspect of the present invention provides the aforesaid process for preparing 2,3,4,4-tetramethylcyclopentanecarbaldehyde (3), the process further comprising:

subjecting 2,3,4,4-tetramethyl-2-cyclopentenone of the following formula (5) to a Wittig reaction with a phosphorus ylide compound of the following formula (6) to form the vinylether compound (4)

(5)

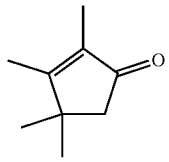

(6)

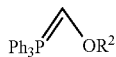

wherein in the general formula (6), R² represents a monovalent hydrocarbon group having 1 to 15 carbon atoms, and Ph represents a phenyl group.

Another aspect of the present invention provides the aforesaid process for preparing 2,3,4,4-tetramethylcyclopentanecarbaldehyde (3), the process further comprising subjecting the 2,3,4,4-tetramethyl-1-cyclopentenecarbaldehyde of the following formula (7) to an acetalization reaction with the alcohol compound of the following formulae (XA) or (XB) in the presence of an acid to form the acetal compound (1)

(7)

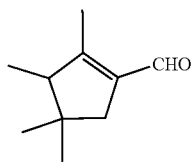

R'OH (XA), wherein R¹ is as defined above;
HOR¹—R¹OH (XB), wherein R¹s represent, independent of each other, as defined above.

Another aspect of the present invention provides the aforesaid process for preparing 2,3,4,4-tetramethylcyclopentanecarbaldehyde (3), the process further comprising subjecting 2,3,4,4-tetramethyl-2-cyclopentenone of the following formula (5) to a Wittig reaction with a phosphorus ylide compound of the following formula (6) to form the vinylether compound (4), and subjecting the vinylether compound (4) to a hydrolysis reaction to form the 2,3,4,4-tetramethyl-1-cyclopentenecarbaldehyde (7)

(5)

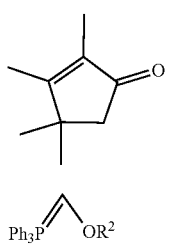

(6)

wherein in the general formula (6), R² represents a monovalent hydrocarbon group having 1 to 15 carbon atoms, and Ph represents a phenyl group.

Another aspect of the present invention provides a novel acetal compound of the following general formula (α):

(α)

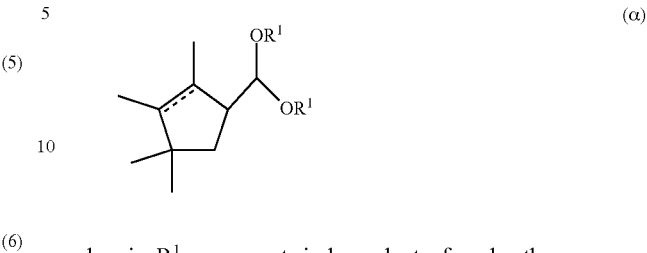

wherein R¹s represent, independent of each other, a monovalent hydrocarbon group having 1 to 6 carbon atoms, or two les may form together a divalent hydrocarbon group, R¹—R¹, having 2 to 12 carbon atoms, and the bonds represented by solid and dotted lines represent single or double bonds.

Another aspect of the present invention provides a novel acetal compound of the following general formula (1), wherein the bond represented by the solid and dotted lines in the general formula (α) is a double bond (1)

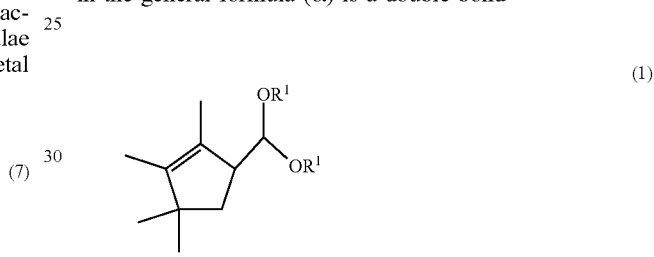

wherein in the general formula (1), R¹ is as defined above for the general formula (α).

Another aspect of the present invention provides a novel acetal compound of the following general formula (2), wherein the bond represented by the solid and dotted lines in the general formula (α) is a single bond (2)

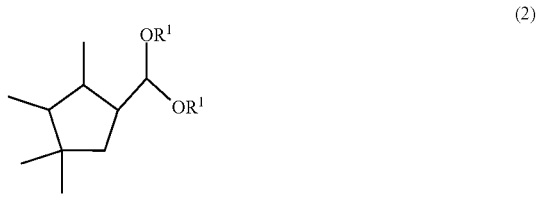

wherein in the general formula (2), R¹ is as defined above for the general formula (α).

The present invention makes it possible to prepare safely, efficiently, selectively, and industrially a (1R*,2R*,3S*)-2,3,4,4-tetramethylcyclopentanecarbaldehyde which is an important preparation intermediate for the preparation of (1R*,2R*,3S*)-(2,3,4,4-tetramethylcyclopentyl)methyl acetate which is promising as a sex pheromone of OMB, which is a serious agricultural pest, for applications such as forecasting outbreaks of the pest and controlling the pest. The present invention also provides the acetal compound (1) and the acetal compound (2) which are useful intermediates for the preparation of 2,3,4,4-tetramethylcyclopentanecarbaldehyde.

DETAILED DESCRIPTION OF THE PREFERRED EMBODIMENTS

Embodiments of the present invention will be explained below in detail. It should be understood that the present invention is not limited to or by the following embodiments. The intermediates, the reagents, and the target compounds represented by the chemical formulae may comprise stereoisomers such as enantiomers and diastereoisomers. Unless otherwise stated, the chemical formulae shall be interpreted to represent all of these isomers. The isomer may be either alone or in combination thereof.

The present inventors have contemplated, as described below, a plan for the synthesis of 2,3,4,4-tetramethylcyclopentanecarbaldehyde (3), which is a target compound of the present invention.

Retrosynthetic analysis is represented, for example, by the following reaction formula for (1R*,2R*,3S*)-2,3,4,4-tetramethylcyclopentanecarbaldehyde (3"), which is a preparation intermediate of a racemic mixture of the sex pheromone of OMB, among 2,3,4,4-tetramethylcyclopentanecarbaldehyde (3).

is anticipated to mainly form the (1R*,2R*,3S*)-2,3,4,4-tetramethylcyclopentanecarbaldehyde (3") which is the target compound.

Step D'

It is thought that (1RS,2R*,3S*)-2,3,4,4-tetramethylcyclopentanecarbaldehyde acetal compound (2') is possible to be synthesized by subjecting the acetal compound of the following general formula (1) to a reduction reaction, more preferably, subjecting the double bond to a hydrogenation reaction. In general, in a hydrogenation reaction, in many cases, a syn addition, in which two hydrogen atoms are added from the same surface to a double bond, has priority, thus, it is anticipated that the cis-form which is the desired configuration would be the main form in a position between position 2 and position 3 of the dimethyl group.

Step C1'

It is thought that the acetal compound (1) is possible to be synthesized by subjecting the 2,3,4,4-tetramethyl-1-cyclopentenecarbaldehyde of the following formula (7) to an acetalization reaction.

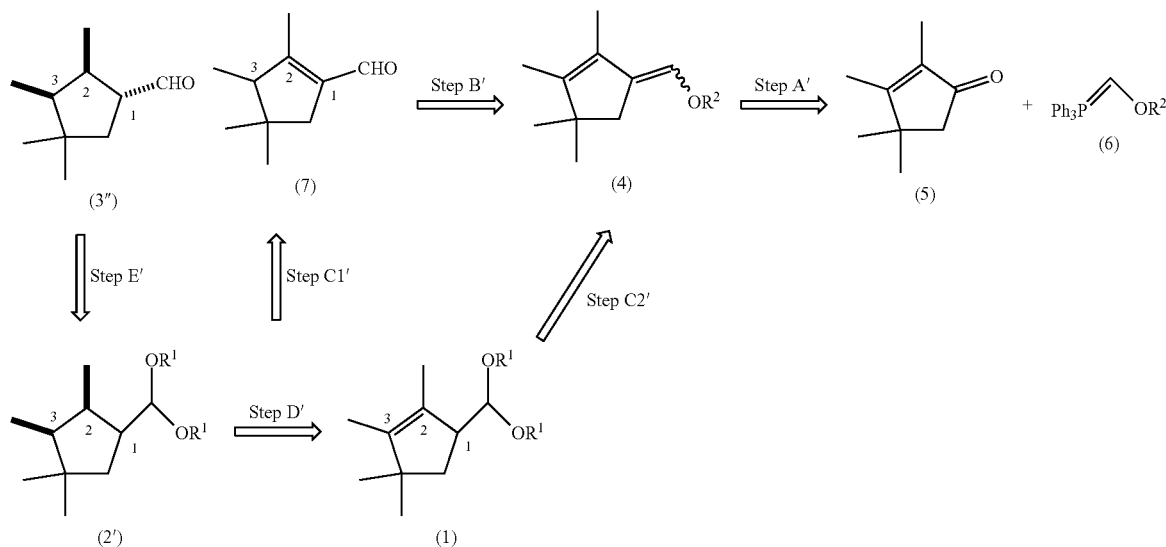

In the general formulae (2') and (1), $R^1$s represent, independent of each other, a monovalent hydrocarbon group having 1 to 6 carbon atoms, or two les may form together a divalent hydrocarbon group, $R^1$—$R^1$, having 2 to 12 carbon atoms. In the general formula (4), $R^2$ represents a monovalent hydrocarbon group having 1 to 15 carbon atoms, and the wavy line represents the E-form, the Z-form, or a mixture thereof. In the general formula (6), $R^2$ is as defined above.

In the reaction scheme of the retrosynthetic analysis shown above, the open arrows represent transforms in the retrosynthetic analysis.

Step E'

It is thought that the (1R*,2R*,3S*)-2,3,4,4-tetramethylcyclopentanecarbaldehyde (3") is possible to be synthesized by subjecting (1RS,2R*,3S*)-2,3,4,4-tetramethylcyclopentanecarbaldehyde acetal compound of the following general formula (2') to a hydrolysis reaction in the presence of an acid. After aldehyde formation, stereoisomerization of the aldehyde occurs under acidic reaction conditions, and converges to a thermodynamically stable 1,2-trans form, and it Step C2'

It is thought that the acetal compound (1) is possible to be synthesized by subjecting the vinylether compound of the following general formula (4) to an acetalization reaction.

Step B'

It is thought that 2,3,4,4-tetramethyl-1-cyclopentenecarbaldehyde (7) is possible to be synthesized by subjecting the vinylether compound (4) to a hydrolysis reaction. It is thought that when the hydrolysis reaction of the vinylether compound (4) forms an aldehyde, the endocyclic double bond easily shifts from a position between position 2 and position 3 of the starting material to a thermodynamically more stable position between position 1 and position 2 on account of conjugation with the carbonyl group of the aldehyde. Thus, isomerization occurs easily.

Step A'

It is thought that the vinylether compound (4) is possible to be synthesized by subjecting 2,3,4,4-tetramethyl-2-cyclopentenone of the following formula (5), which is a known ketone, to a Wittig reaction with a phosphorus ylide compound of the following general formula (6).

In consideration of the reaction scheme of the retrosynthetic analysis mentioned above, an embodiment of the present invention may be depicted by the following chemical reaction scheme.

As an exemplary embodiment of the present invention, steps A to E based on the retrosynthetic analysis will be explained in detail below in the order of Step D, Step E, Step A, Step B, and Step C1 and Step C2.

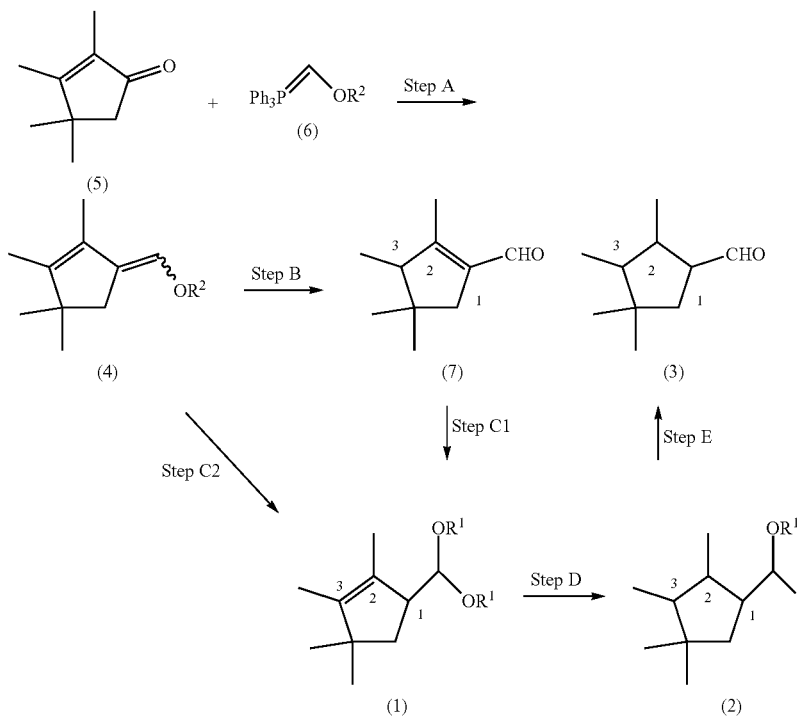

R¹s represent, independent of each other, a monovalent hydrocarbon group having 1 to 6 carbon atoms or two R¹s may form together a divalent hydrocarbon group, R¹—R¹, having 2 to 12 carbon atoms, le represents a monovalent hydrocarbon group having 1 to 15 carbon atoms, and the wavy line represents the E-form, the Z-form, or a mixture thereof.

(Step A) 2,3,4,4-tetramethyl-2-cyclopentenone (5) is subjected to a Wittig reaction with a phosphorus ylide compound (6) to form a vinylether compound (4), as shown in the chemical reaction formula above.

(Step B) Next, the vinylether compound (4) obtained according to Step A is subjected to a hydrolysis reaction to form 2,3,4,4-tetramethyl-1-cyclopentenecarbaldehyde (7).

(Step C1) 2,3,4,4-tetramethyl-1-cyclopentenecarbaldehyde (7) obtained according to Step B is subjected to an acetalization reaction in the presence of an acid to obtain the acetal compound (1) which is the target compound.

(Step C2) The vinylether compound (4) obtained according to Step A or by another method is subjected to an acetalization reaction in the presence of an acid to obtain the acetal compound (1).

(Step D) 2,3,4,4-tetramethylcyclopentanecarbaldehyde acetal compound (2) may be obtained by subjecting the acetal compound (1) obtained according to Step C1 or Step C2 to a hydrogenation reaction.

(Step E) 2,3,4,4-tetramethylcyclopentanecarbaldehyde (3) may be obtained by subjecting 2,3,4,4-tetramethylcyclopentanecarbaldehyde acetal compound (2) obtained according to Step D to a hydrolysis reaction.

[1] Step D

Step D to obtain an acetal compound of the following general formula (2) will be explained below. The acetal compound (2) is obtained by subjecting an acetal compound of the following general formula (1) to a hydrogenation reaction as shown in the following chemical reaction formula.

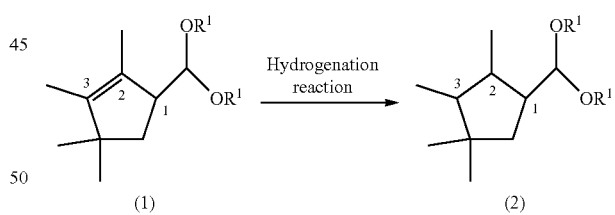

In the general formulae (1) and (2), R¹s represent, independent of each other, as defined above.

First, an acetal compound of the following general formula (1), which is the starting material in Step D, will be explained below.

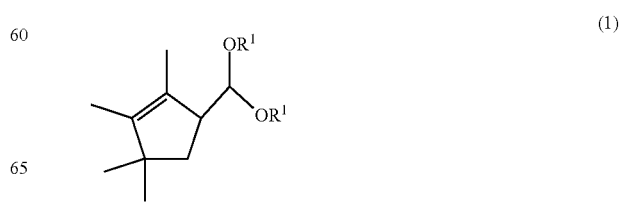

In the general formula (1), les represent, independent of each other, a monovalent hydrocarbon having 1 to 6 carbon atoms, preferably a monovalent hydrocarbon having 1 to 4 carbon atoms, or two les combined with each other to represent a divalent hydrocarbon group having 2 to 12 carbon atoms, preferably 2 to 4 carbon atoms as $R^1$—$R^1$.

Examples of the monovalent hydrocarbon group include linear saturated hydrocarbon groups such as a methyl group, an ethyl group, a propyl group, a butyl group, a pentyl group and a hexyl group; branched saturated hydrocarbon groups such as an isopropyl group, an s-butyl group, a t-butyl group, and an isobutyl group; cyclic saturated hydrocarbon groups such as a cyclohexyl group; and unsaturated hydrocarbon groups such as an allyl group. Preferred are a methyl group, an ethyl group, a propyl group, and a butyl group in view of the yield and the economy.

Examples of the divalent hydrocarbon group of $R^1$—$R^1$ include an ethylene group, a propylene group, a butylene group, a hexylene group, a 1,2-decandiyl group, a trimethylene group, a 2,3-butanediyl group and a 1,2-cyclohexanediyl group. Preferred are an ethylene group, a propylene group and a trimethylene group in view of the yield and/or the economy.

Specific examples of the acetal compound (1) include 2,3,4,4-tetramethyl-2-cyclopentenecarbaldehyde dimethyl acetal, 2,3,4,4-tetramethyl-2-cyclopentenecarbaldehyde diethyl acetal, 2,3,4,4-tetramethyl-2-cyclopentenecarbaldehyde dipropyl acetal, 2,3,4,4-tetramethyl-2-cyclopentenecarbaldehyde dibutyl acetal, 2,3,4,4-tetramethyl-2-cyclopentenecarbaldehyde dipentyl acetal, 2,3,4,4-tetramethyl-2-cyclopentenecarbaldehyde dihexyl acetal, 2,3,4,4-tetramethyl-2-cyclopentenecarbaldehyde diisobutyl acetal, 2,3,4,4-tetramethyl-2-cyclopentenecarbaldehyde diallyl acetal, 2,3,4,4-tetramethyl-2-cyclopentenecarbaldehyde ethylene acetal, 2,3,4,4-tetramethyl-2-cyclopentenecarbaldehyde propylene acetal, 2,3,4,4-tetramethyl-2-cyclopentenecarbaldehyde butylene acetal, 2,3,4,4-tetramethyl-2-cyclopentenecarbaldehyde hexylene acetal, and 2,3,4,4-tetramethyl-2-cyclopentenecarbaldehyde trimethylene acetal. 2,3,4,4-Tetramethyl-2-cyclopentenecarbaldehyde dimethyl acetal, 2,3,4,4-tetramethyl-2-cyclopentenecarbaldehyde diethyl acetal, 2,3,4,4-tetramethyl-2-cyclopentenecarbaldehyde dipropyl acetal, 2,3,4,4-tetramethyl-2-cyclopentenecarbaldehyde dibutyl acetal, 2,3,4,4-tetramethyl-2-cyclopentenecarbaldehyde ethylene acetal, 2,3,4,4-tetramethyl-2-cyclopentenecarbaldehyde propylene acetal, and 2,3,4,4-tetramethyl-2-cyclopentenecarbaldehyde trimethylene acetal are preferred in view of production ease.

The process for preparing the acetal compound (1) will be explained in the following Step A, Step B, Step C1, and Step C2.

Next, the acetal compound (2), which is the target compound of Step D, will be explained below.

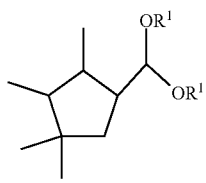

(2)

In the general formula (2), les represent, independent of each other, as defined for the general formula (1).

Specific examples of the acetal compound (2) include 2,3,4,4-tetramethylcyclopentanecarbaldehyde dimethyl acetal, 2,3,4,4-tetramethylcyclopentanecarbaldehyde diethyl acetal, 2,3,4,4-tetramethylcyclopentanecarbaldehyde dipropyl acetal, 2,3,4,4-tetramethylcyclopentanecarbaldehyde dibutyl acetal, 2,3,4,4-tetramethylcyclopentanecarbaldehyde dipentyl acetal, 2,3,4,4-tetramethylcyclopentanecarbaldehyde dihexyl acetal, 2,3,4,4-tetramethylcyclopentanecarbaldehyde diisobutyl acetal, 2,3,4,4-tetramethyl-2-cyclopentenecarbaldehyde diallyl acetal, 2,3,4,4-tetramethylcyclopentanecarbaldehyde ethylene acetal, 2,3,4,4-tetramethyl-2-cyclopentenecarbaldehyde propylene acetal, 2,3,4,4-tetramethylcyclopentanecarbaldehyde butylene acetal, 2,3,4,4-tetramethyl-2-cyclopentenecarbaldehyde hexylene acetal, and 2,3,4,4-tetramethylcyclopentanecarbaldehyde trimethylene acetal. 2,3,4,4-tetramethylcyclopentanecarbaldehyde dimethyl acetal, 2,3,4,4-tetramethylcyclopentanecarbaldehyde diethyl acetal, 2,3,4,4-tetramethylcyclopentanecarbaldehyde dipropyl acetal, 2,3,4,4-tetramethylcyclopentanecarbaldehyde dibutyl acetal, 2,3,4,4-tetramethyl-2-cyclopentenecarbaldehyde ethylene acetal, 2,3,4,4-tetramethylcyclopentanecarbaldehyde propylene acetal, and 2,3,4,4-tetramethylcyclopentanecarbaldehyde trimethylene acetal are preferred in view of production ease.

The hydrogenation reaction may be carried out by reacting the acetal compound (1) with hydrogen in the presence of a hydrogenation catalyst in a solvent, if necessary. The hydrogenation reaction may be carried out with cooling or heating.

Examples of the hydrogenation catalyst include metals (referred also to as a metal catalyst) such as cobalt, nickel, rhodium, palladium, ruthenium, osmium, platinum, iridium, copper and iron and metal oxides (referred also to as a metal oxide catalyst) of these metals; metal hydroxides such as palladium hydroxide and rhodium hydroxide; metal halides such as palladium chloride, ruthenium chloride, and rhodium chloride; and complex compounds such as chloroplatinic acid and chlorotris(triphenylphosphine)rhodium.

The hydrogenation catalyst may be a metal catalyst or a metal oxide catalyst, as listed above, supported on a carrier. Examples of the carrier include carbon, alumina, zeolite, and silica gel. The carrier is preferably carbon. Specific examples of the hydrogenation catalyst supported on carbon include rhodium on carbon, palladium on carbon, ruthenium on carbon, platinum on carbon and palladium hydroxide on carbon. Rhodium on carbon, palladium on carbon, and palladium hydroxide on carbon are particularly preferred.

The hydrogenation catalyst may be used alone or in combination thereof, if necessary. The hydrogenation catalyst may be commercially available one.

An amount of the hydrogenation catalyst may be arbitrarily set as long as a practically sufficient reaction rate is achieved. The amount is preferably as small as possible in view of the economy and is preferably from 0.00001 to 10 mol, more preferably from 0.00001 to 1 mol, more preferably from 0.00001 to 0.5 mol, and even more preferably from 0.00001 to 0.5, mol per mol of the acetal compound (1).

Examples of the solvent used in the hydrogenation reaction include alcohols such as methanol, ethanol, isopropyl alcohol, t-butyl alcohol, benzyl alcohol, methoxyethanol, ethoxyethanol, diethyleneglycol monomethyl ether, and triethyleneglycol monomethyl ether; ethers such as diethyl ether, di-n-butyl ether, tetrahydrofuran, and 1,4-dioxane; hydrocarbons such as hexane, heptane, benzene, toluene, xylene, and cumene; aprotic polar solvents such as N,N- dimethylformamide (DMF), 1,3-dimethyl-2-imidazolidinone (DMI), dimethyl sulfoxide (DMSO), and hexamethylphosphoric triamide (HMPA); nitriles such as acetonitrile and propionitrile; carboxylic acids such as formic acid, acetic acid, and trifluoroacetic acid; and water.

The solvent may be used alone or in combination thereof, if necessary. The solvent may be commercially available one.

An amount of the solvent is preferably from 0.01 part by mass to 100,000 parts by mass, and more preferably 0.1 part by mass to 10,000 parts by mass per 100 parts by mass of the acetal compound (1).

A hydrogen pressure used in the hydrogenation reaction is preferably from normal pressure to 5 MPa.

A reaction temperature of the hydrogenation reaction may be arbitrarily set as long as a practically sufficient reaction rate is achieved. The reaction temperature is preferably from −20° C. to 150° C., and more preferably from 0° C. to 100° C.

A reaction time of the hydrogenation reaction may be arbitrarily set. In view of the yield, it is desirable to monitor progress of the reaction with gas chromatography (GC) and/or thin layer chromatography (TLC) to complete the reaction. The reaction time is typically and preferably from 5 minutes to 240 hours.

When the acetal compound (2) obtained in the hydrogenation reaction has a sufficient purity for a subsequent step, a crude product or a reaction mixture or a reaction mixture filtrate may be used as such in the subsequent step. Alternatively, when it is desired to separate and remove impurities, they may be removed in any purification method used in ordinary organic syntheses, such as distillation and/or various chromatography. The purification is preferably distillation, for example distillation under reduced pressure in view of the industrial economy.

For the preparation of a racemic preparation intermediate of an OMB sex pheromone, the acetal compound of the following general formula (2') in which the dimethyl groups at position 2 and position 3 in the acetal compound (2) are cis-configured, as shown in the following formula is preferred. To preferentially prepare the acetal compound (2'), the hydrogenation catalyst is preferably, a metal such as rhodium or palladium, a metal oxide of these metals, or a metal catalyst or a metal oxide catalyst supported on a carrier such as carbon, alumina, zeolite, or silica gel. A metal catalyst or a metal oxide catalyst supported on a carrier such as carbon is particularly preferred in view of ease of handling, reactivity and/or the economy, and specifically using rhodium on carbon, palladium on carbon or palladium hydroxide on carbon is preferred in view of the compatibility of stereoselectivity and yield.

Generally, in a hydrogenation reaction which uses these hydrogen catalysts, there are many cases when a syn addition in which two hydrogen atoms are added from the same surface to a double bond has priority, and accordingly, it is thought that the cis-form which is the desired configuration would be the main form in a position between position 2 and position 3 of the dimethyl group.

The relative configuration of the two methyl groups at positions 2 and 3 of the acetal compound (2') obtained in Step D is kept in subsequent steps in Step E which is the next step. Therefore, it is very important to increase stereoselectivity in Step D for increasing the diastereomeric ratio of the target compound.

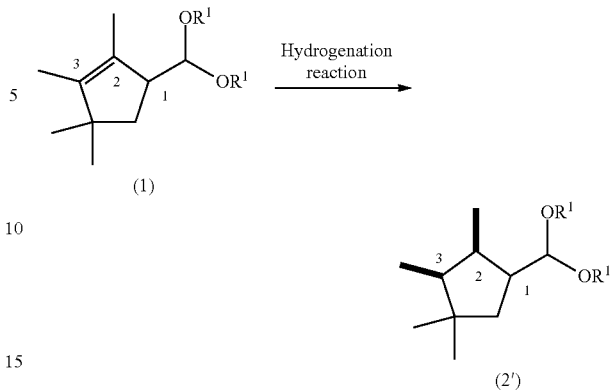

In the general formulae (1) and (2'), les represent, independent of each other, as defined above.

[2] Step E

Step E to prepare 2,3,4,4-tetramethylcyclopentanecarbaldehyde of the following general formula (3) will be explained below. 2,3,4,4-Tetramethylcyclopentanecarbaldehyde (3) is obtained by subjecting the acetal compound (2) obtained in Step D to a hydrolysis reaction as shown in the following chemical reaction formula.

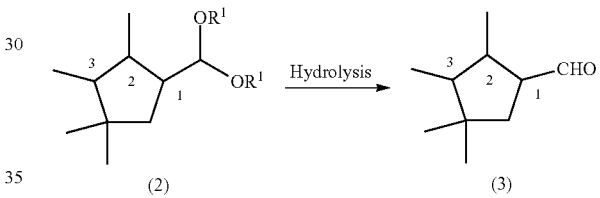

In the general formula (2), les represent, independent of each other, as defined above.

The acetal compound (2), which is the starting material of Step E, is as explained in the above [1].

Next, the following 2,3,4,4-tetramethylcyclopentanecarbaldehyde (3), which is the target compound of Step E, will be explained below.

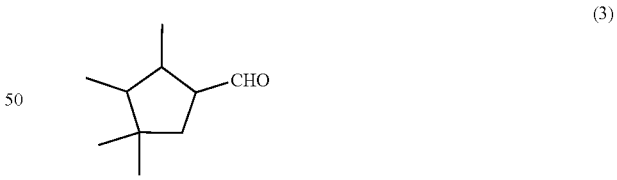

2,3,4,4-Tetramethylcyclopentanecarbaldehyde (3) has four diastereomers as follows: (1R*,2R*,3R*)-2,3,4,4-tetramethylcyclopentanecarbaldehyde (hereinafter, referred also to as (1R*,2R*,3R*)-form); (1R*,2S*,3R*)-2,3,4,4-tetramethylcyclopentanecarbaldehyde (hereinafter, referred also to as the (1R*,2S*,3R*)-form); (1R*,2S*,3S*)-2,3,4,4-tetramethylcyclopentanecarbaldehyde (hereinafter, referred also to as the (1R*,2S*,3S*)-form); and (1R*,2R*,3S*)-2,3,4,4-tetramethylcyclopentanecarbaldehyde of the following formula (3") (hereinafter, referred also to as the (1R*,2R*,3S*)-form (3")). The (1R*,2R*,3S*)-form (3") has the relative configuration same as that of the sex pheromone of OMB.

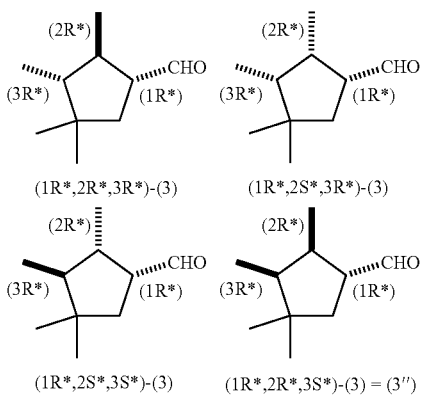

In the formula (3), the bold bond and the hashed bond represent a relative configuration.

In the non-stereoselective preparation, the (1R*,2R*,3S*)-form (3") having the relative configuration same as that of the naturally occurring sex pheromone of OMB is prepared in an expected diastereomeric ratio of only around 25% dr. When the (1R*,2R*,3S*)-form (3") was converted to the sex pheromone of OMB, the active ingredient ratio is low, and there are concerns that contamination with large amounts of such inactive components may have some adverse effects on practical uses. For example, if the diastereomeric ratio decreases by half in the production of an amount of the active component, the total production amount is required to be doubled to obtain the same amount of the active component. Therefore, a higher diastereomeric ratio is advantageous in view of the industrial economy.

As for 2,3,4,4-tetramethylcyclopentanecarbaldehyde (3), the (1R*,2R*,3S*)-form (3") has preferably a diastereomer ratio, dr, of 50% or more, and more preferably 60% or more.

The hydrolysis reaction may be carried out by adding water and an acid and/or a solvent, if necessary, to the acetal compound (2). The hydrogenation reaction may be carried out with cooling or heating.

An amount of the water used in the hydrolysis reaction may be arbitrarily set as long as a practically sufficient reaction rate is achieved. The amount is preferably from 0.1 to 100,000 mol, more preferably from 0.5 to 10,000 mol, and even more preferably from 1 to 1,000 mol, per mol of the acetal compound (2).

The acid used in the hydrolysis reaction is preferably commercially available in large amounts. Examples of the acid include inorganic acids such as hydrochloric acid, hydrobromic acid, hydroiodic acid, sulfuric acid, nitric acid, and phosphoric acid, or salts thereof; organic acids such as formic acid, acetic acid, propionic acid, oxalic acid, trifluoroacetic acid, methanesulfonic acid, benzenesulfonic acid, p-toluenesulfonic acid, trifluoromethanesulfonic acid, and naphthalenesulfonic acid, or salts thereof; Lewis acids such as lithium tetrafluoroborate, boron trifluoride, boron trichloride, boron tribromide, aluminum trichloride, zinc chloride, zinc bromide, zinc iodide, tin tetrachloride, tin tetrabromide, tin dichloride, titanium tetrachloride, titanium tetrabromide, and trimethylsilyl iodide; oxides such as alumina, silica gel, and titania; various cation exchange resins; and minerals such as montmorillonite. Preferred are hydrochloric acid, sulfuric acid, nitric acid, phosphoric acid, formic acid, acetic acid, oxalic acid, and p-toluenesulfonic acid in view of the economy and/or reactivity.

The acid may be used alone or in combination thereof, if necessary. The acid may be commercially available one.

An amount of the acid may be arbitrarily set as long as a practically sufficient reaction rate is achieved. The amount is preferably as small as possible in view of the economy, and is preferably from 0.00001 to 10,000 mol, more preferably from 0.0001 to 1,000 mol, and even more preferably from 0.001 to 100 mol, per mol of the acetal compound (2).

As described in Step E' of the retrosynthetic analysis, the inventor anticipated that after aldehyde formation, stereoisomerization of the aldehyde would occur under acidic reaction conditions, and converge to a thermodynamically stable 1,2-trans form, and mainly form the desired (1R*,2R*,3S*)-form (3"); and in fact this was the actual case. Therefore, an acid is preferably used in the hydrolysis reaction, in view of the preparation of the (1R*,2R*,3S*)-form (3") which is the preparation intermediate of the racemic mixture of the sex pheromone of OMB.

A solvent other than water may be incorporated in the hydrolysis reaction.

Examples of the solvent include diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; ketones such as acetone and methyl ethyl ketone; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); nitriles such as acetonitrile and propionitrile; esters such as ethyl acetate and n-butyl acetate; and alcohols such as methanol, ethanol, and t-butyl alcohol. The solvent is preferably an ether such as diethyl ether or tetrahydrofuran or a mixed solvent containing an ether.

The solvent may be used alone or in combination thereof, if necessary. The solvent may be commercially available one.

An amount of the solvent is preferably from 10 g to 10,000 g per mol of the acetal compound (2).

A reaction temperature of the hydrolysis reaction depends on the reaction conditions, and is preferably from −78 to 160° C., more preferably from −50 to 140° C., and even more preferably from −30 to 120° C.

A reaction time of the hydrolysis reaction may be arbitrarily set. In view of the yield, it is desirable to monitor progress of the reaction with gas chromatography (GC) and/or silica gel thin layer chromatography (TLC) to complete the reaction. The reaction time is typically and preferably from 0.5 to 100 hours.

The hydrolysis reaction may be done while removing an alcohol compound $R^1$—OH, wherein $R^1$ is as defined for the general formula (1), which is a reaction side product out of the reaction system by distillation or other methods.

When 2,3,4,4-tetramethylcyclopentanecarbaldehyde (3) obtained in the hydrolysis reaction has a sufficient purity for a subsequent step, a crude product or a reaction mixture filtrate may be used as such in the subsequent step. Alternatively, when it is desired to separate and remove impurities, they may be removed in any purification method used in ordinary organic syntheses, such as distillation and/or various chromatography. The purification is preferably distillation, for example distillation under reduced pressure, in view of the industrial economy.

Among the four possible diastereomers of 2,3,4,4-tetramethylcyclopentanecarbaldehyde (3), specifically, (1R*,2R*,3S*)-form of the following formula (3") is remarkably valuable industrially. This is because the (1R*,2R*,3S*)- form (3") may be easily converted to (1R*,2R*,3S*)-(2,3,4,4-tetramethylcyclopentyl)methyl acetate which has been already confirmed to have an attracting activity for males of OMB as mentioned above.

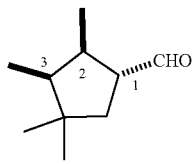

(3")

In the formula (3"), the bold bond and the hashed bond represent a relative configuration.

According to the process for preparing of the present invention, for example, the (1R*,2R*,3S*)-form (3") having the relative configuration same as that of the naturally occurring sex pheromone of OMB may stereoselectively and easily be prepared among the four possible diastereomers of 2,3,4,4-tetramethylcyclopentanecarbaldehyde (3) in a selectivity of 50% dr or more by the hydrogenation reaction using the acetal compound (1) as a reaction substrate, and preferably, using rhodium, palladium, ruthenium, platinum, or oxides thereof, or a metal catalyst or metal oxide catalyst supported on a carrier such as carbon, alumina, zeolite, or silica gels as the hydrogenation catalyst, and In view of the ease of handling, reactivity and/or the economy, preferably using a metal catalyst or metal oxide catalyst supported on a carrier such as carbon, and performing a hydrogenation reaction which specifically uses rhodium on carbon, palladium on carbon, ruthenium on carbon, platinum on carbon or palladium hydroxide on carbon.

By adjusting the reaction conditions of the hydrogenation reaction of Step D and optionally the hydrolysis reaction of Step E it is also possible to prepare diastereomer ratio (dr) of the (1R*,2R*,3S*)-form (3") diastereomer of 60% or more.

[3] Step A

Step A to prepare a vinylether compound of the following general formula (4) will be explained below. The vinylether compound (4) may be obtained by subjecting 2,3,4,4-tetramethyl-2-cyclopentenone of the following formula (5) to a Wittig reaction with a phosphorus ylide compound of the following formula (6), as shown in the following chemical reaction formula.

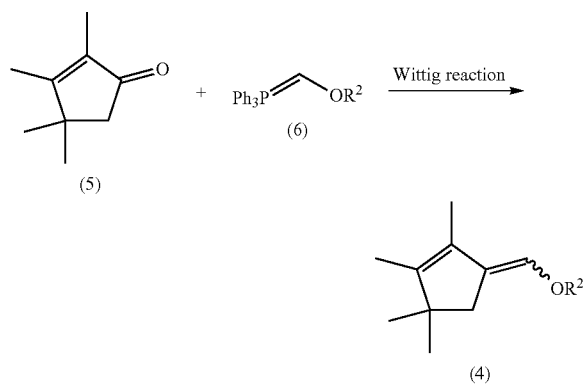

In the general formula, $R^2$ represents a monovalent hydrocarbon group having 1 to 15 carbon atoms. Ph represents a phenyl group. The wavy line represents the E-form, the Z-form, or a mixture thereof.

2,3,4,4-Tetramethyl-2-cyclopentenone (5), which is the starting material of Step A, is a known compound and may be easily prepared in one step, for example, according to a method described in Bull. Soc. Chem. Fr., 2981 (1970) as shown in the Non-Patent Literature 5 or J. Am. Chem. Soc., 113, 8062 (1991) as shown in the Non-Patent Literature 6.

Next, the phosphorus ylide compound (6) will be explained below.

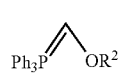

(6)

$R^2$ in the general formula (6) represents a monovalent hydrocarbon having 1 to 15 carbon atoms, preferably 1 to 7 carbon atoms, more preferably 1 to 4 carbon atoms, and Ph represents a phenyl group.

Examples of the monovalent hydrocarbon group in general formula (6) include linear saturated hydrocarbon groups such as a methyl group, an ethyl group, a propyl group, a butyl group, a pentyl group, a hexyl group, a decyl group, an undecyl group, and a pentadecyl group; branched saturated hydrocarbon groups such as an isopropyl group, an s-butyl group, a t-butyl group, and an isobutyl group; cyclic saturated hydrocarbon groups such as a cyclohexyl group; unsaturated hydrocarbon groups such as an allyl group; aryl groups such as a phenyl group, and aralkyl groups such as a benzyl group, and a phenethyl group. Preferred are a methyl group, an ethyl group, a phenyl group and a benzyl group in view of the economy. A part of the hydrogen atoms in the hydrocarbon group may be substituted and is preferably substituted with a halogen group, an alkoxy group having 1 to 4 carbon atoms, an alkylthio group, and a trialkylsilyl group. Substituted hydrocarbon groups are more specifically a 2-(trimethylsilyl)ethyl group, a 2-methoxyethyl group, a 2-(methylthio)ethyl group, a chlorophenyl group, and a methoxyphenyl group.

Specific examples of the phosphorus ylide compound (6) include (methoxymethylene)triphenylphosphorane, (ethoxymethylene)triphenylphosphorane, (propoxymethylene)triphenylphosphorane, (butoxymethylene)triphenylphosphorane, (decyloxymethylene)triphenylphosphorane, (pentadecyloxymethylene)triphenylphosphorane, (isopropoxymethylene)triphenylphosphorane, (cyclohexyloxymethylene)triphenylphosphorane, (allyloxymethylene)triphenylphosphorane, (phenoxymethylene)triphenylphosphorane, (benzyloxymethylene)triphenylphosphorane, [(2-methoxyethoxy)methylene]triphenylphosphorane, [2-(methylthio)ethoxymethylene]triphenylphosphorane, [(4-chlorophenoxy)methylene]triphenylphosphorane, and [(4-methoxyphenoxy)methylene]triphenylphosphorane.

(Methoxymethylene)triphenylphosphorane, (ethoxymethylene)triphenylphosphorane, (phenoxymethylene)triphenylphosphorane, and (benzyloxymethylene)triphenylphosphorane are preferred in view of the availability of raw materials and/or the production cost.

A process for preparing the phosphorus ylide compound (6) is not particularly limited, and the phosphorus ylide compound (6) is obtained, for example, by subjecting a triphenylphosphonium halide compound (101) to a dehydrohalogenation reaction in the presence of a base as shown in the following reaction formula.

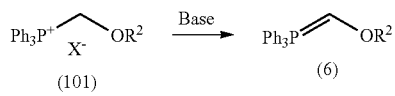

R² in the general formula (101) is as defined for the general formula (6). X represents a halogen atom, preferably a chlorine atom, a bromine atom, or an iodine atom. Ph represents a phenyl group.

Specific examples of the triphenylphosphonium halide compound (101) include (methoxymethyl)triphenylphosphonium chloride, (methoxymethyl)triphenylphosphonium bromide, (methoxymethyl triphenylphosphonium)iodide, (ethoxymethyl)triphenylphosphonium chloride, (butoxymethyl)triphenylphosphonium chloride, (pentadecyloxymethyl)triphenylphosphonium chloride, (isopropoxymethyl)triphenylphosphonium chloride, (cyclohexyloxymethyl) triphenylphosphonium chloride, (allyloxymethyl) triphenylphosphonium chloride, (phenoxymethyl) triphenylphosphonium chloride, (benzyloxymethyl) triphenylphosphonium chloride, triphenyl[2-(trimethylsilyl)ethoxymethylene]phosphonium chloride, [(2-methoxyethoxy)methyl)triphenylphosphonium chloride, [2-(methylthio)ethoxymethyl)triphenylphosphonium chloride, [(4-chlorophenoxy)methyl)triphenylphosphonium chloride, and [(4-methoxyphenoxy)methyl)triphenylphosphonium chloride.

The triphenylphosphonium halide compound (101) may be commercially available one, or may be prepared by a reaction between a halide of the following general formula (102) and triphenylphosphine, i.e., PPh₃, to form the quaternary phosphonium salt.

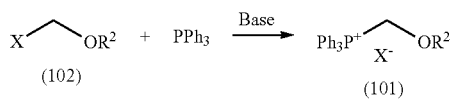

In the general formulae, R², X and Ph are as defined above.

Specific examples of the halide (102) include chloromethyl methyl ether, bromomethyl methyl ether, iodomethyl methyl ether, chloromethyl ethyl ether, butyl chloromethyl ether, chloromethyl pentadecyl ether, chloromethyl isopropyl ether, chloromethyl cyclohexyl ether, allyl chloromethyl ether, chloromethyl phenyl ether, benzyl chloromethyl ether, 2-methoxyethoxymethyl chloride, chloromethyl 2-(trimethylsilyl)ethyl ether, chloromethyl 2-(methylthio)ethoxymethyl ether, chloromethyl 4-chlorophenyl ether, and chloromethyl 4-methoxyphenyl ether.

In the preparation of the triphenylphosphonium halide compound (101), a metal halide and/or a quaternary onium salt may be added to accelerate the reaction.

Examples of the metal halide include lithium iodide, sodium iodide, potassium iodide, lithium bromide, sodium bromide, and potassium bromide.

Examples of the quaternary onium salt include tetraethylammonium bromide, tetrabutylammonium bromide, tetrabutylphosphonium bromide, tetraethylammonium iodide, tetrabutylammonium iodide, and tetrabutylphosphonium iodide.

In the preparation of the triphenylphosphonium halide compound (101), the reaction may be carried out in basic conditions by adding bicarbonates such as lithium bicarbonate, sodium bicarbonate, and potassium bicarbonate; carbonates such as lithium carbonate, sodium carbonate, and potassium carbonate; hydroxide salts such as lithium hydroxide, sodium hydroxide, and potassium hydroxide; or organic bases such as triethylamine, diisopropylethylamine, tributylamine, N,N-dimethylaniline, N,N-diethylaniline, pyridine, 4-dimethylaminopyridine, quinoline, pyrrolidine, piperidine, collidine, lutidine, and morpholine.

The triphenylphosphonium halide compound (101) is preferably prepared in a solvent.

Examples of the solvent include ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; aprotic polar solvents such as N,N-dimethylformamide, N,N-dimethylacetamide, N-methylpyrrolidone, 1,3-dimethyl-2-imidazolidinone, dimethyl sulfoxide, and hexamethylphosphoric triamide; nitriles such as acetonitrile and propionitrile; esters such as ethyl acetate and n-butyl acetate; and alcohols such as methanol, ethanol, and t-butyl alcohol.

The solvent may be used alone or in combination thereof, if necessary. The solvent may be commercially available one.

An amount of the solvent is preferably from 10 g to 10,000 g per mol of the halide (102).

A reaction temperature in the preparation of the triphenylphosphonium halide compound (101) may be appropriately selected, depending on starting materials. Typically, the reaction temperature is from −10° C. to 180° C., preferably from 0° C. to 160° C., and more preferably from 10° C. to 140° C.

A reaction time of the preparation of the triphenylphosphonium halide compound (101) may be arbitrarily set. In view of the yield, it is desirable to monitor progress of the reaction with gas chromatography (GC) and/or silica gel thin layer chromatography (TLC) to complete the reaction. The reaction time is typically and preferably from 0.5 to 60 hours.

Examples of the base used in the preparation of the phosphorus ylide compound (6) include metal alkoxides such as sodium methoxide, sodium ethoxide, sodium t-butoxide, sodium t-amiloxide, lithium methoxide, lithium ethoxide, lithium t-butoxide, lithium t-amiloxide, potassium methoxide, potassium ethoxide, potassium t-butoxide, and potassium t-amiloxide; organometallic reagents such as methyllithium, ethyllithium, n-butyllithium, methylmagnesium chloride, sodium acetylide, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; and metal hydrides such as sodium hydride, potassium hydride, and calcium hydride.

The base may be used alone or in combination thereof, if necessary, and is chosen, depending on the type of the triphenylphosphonium halide compound (101) which is a substrate, and/or reactivity and/or reaction yield. The base may be commercially available one.

An amount of the base used in the preparation of the phosphorus ylide compound (6) is preferably from 0.7 mol to 5 mol per mol of the triphenylphosphonium halide compound (101).

The solvent used in the preparation of the phosphorus ylide compound (6) may be same as that used in the preparation of the triphenylphosphonium halide compound (101).

A reaction temperature in the preparation of the phosphorus ylide compound (6) is preferably from −78 to 50° C., and more preferably from −78° C. to 35° C.

A reaction time of the preparation of the phosphorus ylide compound (6) is preferably from 5 minutes to 18 hours, and more preferably from 5 minutes to 10 hours, in view of the stability of the reactants.

Next, the vinylether compound (4), which is the target compound of Step A, will be explained below.

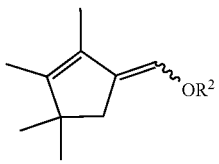

(4)

$R^2$ in general formula (4) is as defined for the general formula (6), and the wavy line represents the E-form, the Z-form, or a mixture thereof.

Specific examples of the vinylether compound (4) include 4-(methoxymethylene)-1,1,2,3-tetramethyl-2-cyclopentene, 4-(ethoxymethylene)-1,1,2,3-tetramethyl-2-cyclopentene, 4-(propoxymethylene)-1,1,2,3-tetramethyl-2-cyclopentene, 4-(butoxymethylene)-1,1,2,3-tetramethyl-2-cyclopentene, 4-(pentadecyloxymethylene)-1,1,2,3-tetramethyl-2-cyclopentene, 4-(isopropoxymethylene)-1,1,2,3-tetramethyl-2-cyclopentene, 4-(cyclohexyloxymethylene)-1,1,2,3-tetramethyl-2-cyclopentene, 4-(allyloxymethylene)-1,1,2,3-tetramethyl-2-cyclopentene, 4-(phenoxymethylene)-1,1,2,3-tetramethyl-2-cyclopentene, 4-(benzyloxymethylene)-1,1,2,3-tetramethyl-2-cyclopentene, 4-[2-(trimethylsilyl)ethoxymethylene]-1,1,2,3-tetramethyl-2-cyclopentene, 4-[(2-methoxyethoxy)methylene]-1,1,2,3-tetramethyl-2-cyclopentene, 4-[2-(methylthio)ethoxymethylene]-1,1,2,3-tetramethyl-2-cyclopentene, 4-[(4-chlorophenoxy)methylene]-1,1,2,3-tetramethyl-2-cyclopentene, and 4-[(4-methoxyphenoxy)methylene]-1,1,2,3-tetramethyl-2-cyclopentene. Preferred are 4-(methoxymethylene)-1,1,2,3-tetramethyl-2-cyclopentene, 4-(ethoxymethylene)-1,1,2,3-tetramethyl-2-cyclopentene, 4-(phenoxymethylene)-1,1,2,3-tetramethyl-2-cyclopentene, and 4-(benzyloxymethylene)-1,1,2,3-tetramethyl-2-cyclopentene in view of the availability of raw materials and/or the cost of production.

The Wittig reaction may be carried out in a solvent by adding 2,3,4,4-tetramethyl-2-cyclopentenone (5). The Wittig reaction may be carried out with cooling or heating.

An amount of 2,3,4,4-tetramethyl-2-cyclopentenone (5) used in the Wittig reaction is from 0.1 mol to 5 mol, preferably from 0.2 mol to 3 mol, per theoretical mol of the phosphorus ylide compound (6).

The solvent used in the Wittig reaction may be same as that used in the preparation of the triphenylphosphonium halide compound (101).

The solvent may be used alone or in combination thereof, if necessary. The solvent may be commercially available one.

An amount of the solvent used in the Wittig reaction is preferably from 10 g to 10,000 g per theoretical mol of the phosphorus ylide compound (6).

A reaction temperature of the Wittig reaction is preferably from −78° C. to 50° C., and more preferably from −50° C. to 35° C.

A reaction time of the Wittig reaction may be arbitrarily set. In view of the yield, it is desirable to monitor progress of the reaction with gas chromatography (GC) and/or silica gel thin layer chromatography (TLC) to complete the reaction. The reaction time is typically and preferably from 0.5 to 24 hours.

When the vinylether compound (4) obtained in the Wittig reaction has a sufficient purity for a subsequent step, a crude product or a reaction mixture or a reaction mixture filtrate may be used as such in the subsequent step. Alternatively, when it is desired to separate and remove impurities, they may be removed in any purification method used in ordinary organic syntheses, such as distillation and/or various chromatography. The purification is preferably distillation, for example distillation under reduced pressure, in view of the industrial economy.

The vinylether compound (4) obtained in the Wittig reaction has two geometric isomers, the E-form and Z-form, on account of the geometrical isomerism of the exocyclic double bond. Thus, the vinylether compound (4) is usually present as a mixture of the two isomers, and the mixture may be used as such in a subsequent step without the need to separate the geometric isomers.

[4] Step B

Step B to prepare 2,3,4,4-tetramethyl-1-cyclopentenecarbaldehyde of the following formula (7) will be explained below. 2,3,4,4-Tetramethyl-1-cyclopentenecarbaldehyde (7) is obtained by subjecting the vinylether compound (4) obtained in Step A to hydrolysis, as shown in the following chemical reaction formula.

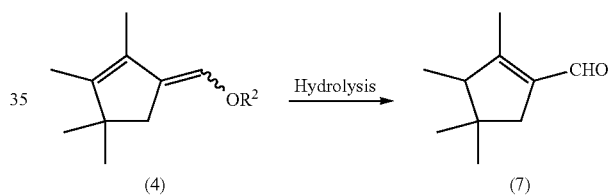

(4)        (7)

$R^2$ in the general formula (4) is as defined above. The wavy line represents the E-form, the Z-form, or a mixture thereof.

The vinylether compound (4), which is the starting material of Step B, is as described in [3].

Next, 2,3,4,4-tetramethyl-1-cyclopentenecarbaldehyde (7), which is the target compound of Step B, is represented by the following formula (7).

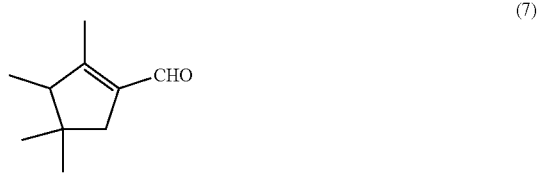

(7)

The hydrolysis reaction may be carried out by adding water and, if necessary, an acid and/or solvent to the vinylether compound (4). The hydrolysis reaction may be carried out with cooling or heating.

An amount of the water used in the hydrolysis reaction may be arbitrarily set as long as a practically sufficient reaction rate is achieved. The amount is preferably from 0.1 to 100,000 mol, more preferably from 0.5 to 10,000 mol, and even more preferably from 1 to 1,000 mol, per mol of the vinylether compound (4).

The acid used in the hydrolysis reaction is preferably commercially available in large amounts. Examples of the acid include inorganic acids such as hydrochloric acid, hydrobromic acid, hydroiodic acid, sulfuric acid, nitric acid, and phosphoric acid, or salts thereof; organic acids such as formic acid, acetic acid, propionic acid, oxalic acid, trifluoroacetic acid, methanesulfonic acid, benzenesulfonic acid, p-toluenesulfonic acid, trifluoromethanesulfonic acid, and naphthalenesulfonic acid, or salts thereof; Lewis acids such as lithium tetrafluoroborate, boron trifluoride, boron trichloride, boron tribromide, aluminum trichloride, zinc chloride, zinc bromide, zinc iodide, tin tetrachloride, tin tetrabromide, tin dichloride, titanium tetrachloride, titanium tetrabromide, and trimethylsilyl iodide; oxides such as alumina, silica gel, and titania; various cation exchange resins; and minerals such as montmorillonite. Preferred are hydrochloric acid, sulfuric acid, nitric acid, phosphoric acid, formic acid, acetic acid, oxalic acid, and p-toluenesulfonic acid in view of the economy and/or reactivity.

The acid may be used alone or in combination thereof, if necessary. The acid may be commercially available one.

An amount of the acid may be arbitrarily set as long as a practically sufficient reaction rate is achieved. The amount is preferably as small as possible in view of the economy, and is preferably from 0.00001 to 10,000 mol, more preferably from 0.0001 to 1,000 mol, and even more preferably from 0.001 to 100 mol, per mol of the vinylether compound (4).

A solvent other than water may be incorporated in the hydrolysis reaction.

Examples of the solvent include ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; ketones such as acetone and methyl ethyl ketone; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); nitriles such as acetonitrile and propionitrile; esters such as ethyl acetate and n-butyl acetate; and alcohols such as methanol, ethanol, and t-butyl alcohol. The solvent is preferably an ether such as diethyl ether or tetrahydrofuran or a mixed solvent containing an ether.

The solvent may be used alone or in combination thereof. The solvent may be commercially available one.

An amount of the solvent is preferably from 10 g to 10,000 g, per mol of the vinylether compound (4).

A reaction temperature in the hydrolysis reaction depends on the reaction conditions, and is preferably from −78 to 160° C., more preferably from −50 to 140° C., and even more preferably from −30 to 120° C.

A reaction time of the hydrolysis reaction may be arbitrarily set. In view of the yield, it is desirable to monitor progress of the reaction with gas chromatography (GC) and/or silica gel thin layer chromatography (TLC) to complete the reaction. The reaction time is typically and preferably from 0.5 to 100 hours.

It is thought that when the hydrolysis reaction of the vinylether compound (4) forms an aldehyde, the double bond originally at position 2 shifts to thermodynamically more stable position 1 on account of conjugation with the carbonyl group of the aldehyde and easily causes isomerization so as to mainly form 2,3,4,4-tetramethyl-1-cyclopentenecarbaldehyde (7).

In the hydrolysis reaction, an alcohol $R^2OH$, which is a side product, may react with the vinylether compound (4), which is the starting material, or with 2,3,4,4-tetramethyl-1-cyclopentenecarbaldehyde (7), which is the product, to form an undesired acetal compound as a byproduct. To prevent the by-production of the undesired acetal compound, the hydrolysis reaction may be done while removing the resulting alcohol $R^2OH$ out of the reaction system by distillation or other methods.

When 2,3,4,4-tetramethyl-1-cyclopentenecarbaldehyde (7) obtained in the hydrolysis reaction has a sufficient purity for a subsequent step, a crude product or a reaction mixture filtrate may be used as such in the subsequent step. Alternatively, when it is desired to separate and remove impurities such as possibly intermixed regioisomers on the double bond, they may be removed in any purification method used in ordinary organic syntheses, such as distillation and/or various chromatography. The purification is preferably distillation, for example distillation under reduced pressure, in view of the industrial economy.

[5] Step C1 and Step C2

Steps C1 and C2 to prepare the acetal compound of the following general formula (1) will be explained below.

The acetal compound (1) may be prepared by the following two processes: Step C1 and Step C2 as shown in the following chemical reaction formula. In Step C1, 2,3,4,4-tetramethyl-1-cyclopentenecarbaldehyde (7) is subjected to an acetalization reaction with an alcohol compound of the following formulae (XA) or (XB) in the presence of an acid. In Step C2, the vinylether compound (4) is subjected to an acetalization reaction with an alcohol compound of the following formulae (XA) or (XB) in the presence of an acid.

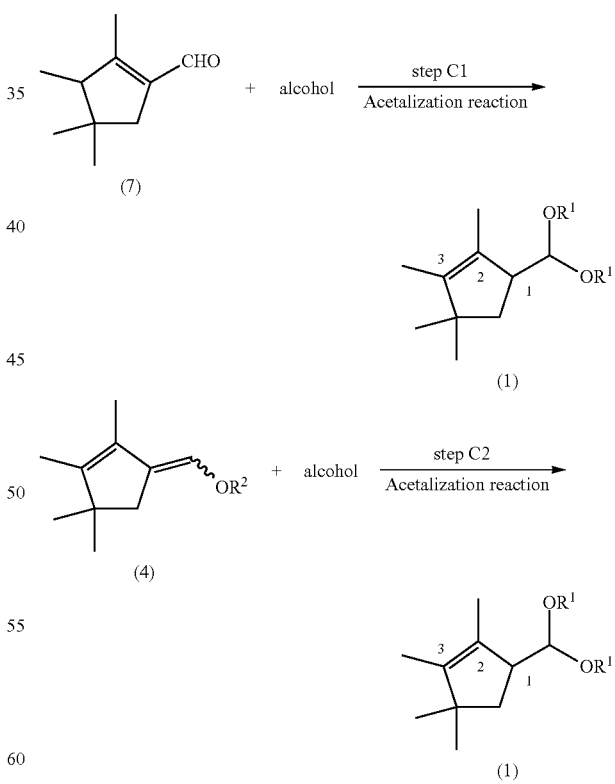

In the general formula, $R^1$ and $R^2$ are as defined above.
R'OH (XA), wherein les represent, independent of each other, as defined above;
HOR$^1$—R$^1$OH (XB), wherein les represent, independent of each other, as defined above.

2,3,4,4-Tetramethyl-1-cyclopentenecarbaldehyde (7), which is the starting material of Step C1, is as explained in [4] above.

The vinylether compound (4), which is the starting material of Step C2, is as explained in [3] above.

The acetal compound (1), which is the target compound of Step C1 and Step C2, is as explained in [1] above.

The acetalization reaction may be carried out by adding a solvent if necessary. The acetalization reaction may be carried out with cooling or heating. The preferred reaction conditions are similar with those in both Step C1 and Step C2 and are explained below.

The alcohol compound used in the acetalization reaction is of the following general formula (XA) or (XB).

$R^1OH$ (XA) or, $HOR^1-R^1OH$ (XB).

$R^1$ in general formula (XA) is as defined for the general formula (1).

$R^1$s in general formula (XB) represent, independent of each other, as defined for the general formula (1).

Specific examples of $R^1OH$ (XA) include methanol, ethanol, 1-propanol, 2-propanol, 1-butanol, 2-butanol, isobutyl alcohol, 1-pentanol, isoamyl alcohol, 1-hexanol, and allyl alcohol. In view of the reactivity, a primary alcohol is more preferred, and specifically, methanol and ethanol are particularly preferred.

Specific examples of $HOR^1-R^1OH$ (XB) include ethylene glycol, propylene glycol, butylene glycol, trimethylene glycol, 2,3-butanediol, 1,2-cyclohexanediol, and 1,2-dodecanediol. In view of the reactivity, ethylene glycol, propylene glycol and trimethylene glycol are preferred, and ethylene glycol is particularly preferred.

An amount of the alcohol compound (XA) or (XB) is preferably from 1 to 100,000 mol, more preferably from 2 to 10,000 mol, and even more preferably from 5 to 1,000 mol, per mol of the vinylether compound (4) or 2,3,4,4-tetramethyl-1-cyclopentenecarbaldehyde (7).

The acid used in the acetalization reaction is preferably commercially available in large amounts. Examples of the acid include inorganic acids such as hydrochloric acid, hydrobromic acid, hydroiodic acid, sulfuric acid, nitric acid, and phosphoric acid, or salts thereof; organic acids such as formic acid, acetic acid, propionic acid, oxalic acid, trifluoroacetic acid, methanesulfonic acid, benzenesulfonic acid, p-toluenesulfonic acid, and naphthalenesulfonic acid, or salts thereof; Lewis acids such as lithium tetrafluoroborate, boron trifluoride, boron trichloride, boron tribromide, aluminum trichloride, zinc chloride, zinc bromide, zinc iodide, tin tetrachloride, tin tetrabromide, tin dichloride, titanium tetrachloride, titanium tetrabromide, and trimethylsilyl iodide; oxides such as alumina, silica gel, and titania; various cation exchange resins; and minerals such as montmorillonite. Preferred are hydrochloric acid, sulfuric acid, nitric acid, phosphoric acid, formic acid, acetic acid, oxalic acid, and p-toluenesulfonic acid in view of the economy and/or reactivity.

The acid may be used alone or in combination thereof, if necessary. The acid may be commercially available one.

An amount of the acid may be arbitrarily set as long as a practically sufficient reaction rate is achieved. The amount is preferably from 0.00001 to 10,000 mol, more preferably from 0.0001 to 1,000 mol, and even more preferably from 0.001 to 100 mol, per mol of 2,3,4,4-tetramethyl-1-cyclopentenecarbaldehyde (7) or the vinylether compound (4) which is the substrate.

When a solvent is used in the acetalization reaction, the examples of the solvent include water; ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); nitriles such as acetonitrile and propionitrile; esters such as ethyl acetate and n-butyl acetate; and alcohols such as methanol, ethanol, and t-butyl alcohol.

The solvent may be used alone or in combination thereof, if necessary. The solvent may be commercially available one.

An amount of the solvent is preferably from 10 g to 10,000 g per mol of 2,3,4,4-tetramethyl-1-cyclopentenecarbaldehyde (7) or the vinylether compound (4).

A reaction temperature of the acetalization reaction depends on the reaction conditions, and is preferably from −20 to 120° C., and more preferably from 0 to 100° C.

A reaction time of the acetalization reaction may be arbitrarily set. In view of the yield, it is desirable to monitor progress of the reaction with gas chromatography (GC) and/or silica gel thin layer chromatography (TLC) to complete the reaction, is typically and preferably from 0.5 to 100 hours.

When the acetal compound (1) obtained in the acetalization reaction has a sufficient purity for a subsequent step, a crude product or a reaction mixture filtrate may be used as such in the subsequent step. Alternatively, when it is desired to separate and remove impurities, they may be removed in any purification method used in ordinary organic syntheses, such as distillation and/or various chromatography. The purification is preferably distillation, for example distillation under reduced pressure, in view of the industrial economy.

EXAMPLES

The present invention will be described with reference to the following Examples. It should be noted that the present invention is not limited to or by the Examples.

The term "purity" as used herein means an area percentage in gas chromatography (GC), unless otherwise specified. The term "product ratio" means a ratio of area percentages in GC.

The term "yield" is calculated from the area percentages determined by GC.

In the Examples, monitoring of the reactions and calculation of the yields were carried out essentially in the following GC conditions.

GC conditions: GC equipment: SHIMADZU GC-2014, capillary column: DB-5, 0.25 mm in internal diameter×0.25 μm in thickness×30 m in length, carrier gas: He, detector: FID, column temperature: elevated from 80° C. in a rate of +5° C./minute, inlet temperature: 230° C.

Note that, purities of raw materials, products, and intermediates were determined by gas chromatography (GC) and expressed as % GC.

The yield was calculated according to the following equation in consideration of purities (% GC) of a starting material and a product.

Yield (%)={[(weight of a product obtained by a reaction×% GC)/molecular weight of a product]÷[(weight of a starting material in a reaction×% GC)/molecular weight of a starting material]}×100

The term "crude yield" refers to a yield of a crude product obtained without purification.

A sample for measuring the spectrum of the compound was obtained by purifying a crude product, if necessary.

In the following chemical structure, Me represents a methyl group, Ph represents a phenyl group, and the wavy line represents the E-form, the Z-form, or a mixture thereof.

Example 1: Synthesis of 4-(Methoxymethylene)-1,1,2,3-Tetramethyl-2-Cyclopentene (4a) (4: R²=Methyl Group)

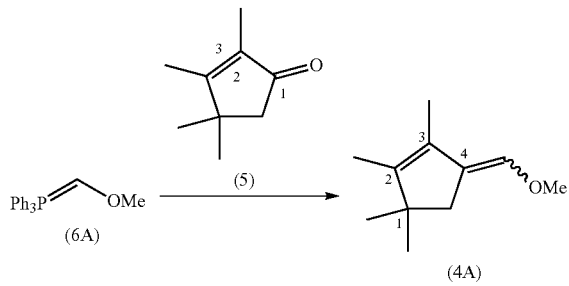

To a mixture of potassium tert-butoxide (183 g) and tetrahydrofuran (847 g) was added (methoxymethyl)triphenylphosphonium chloride (588 g) under nitrogen atmosphere with ice-cooling and stirring, and stirred for 100 minutes to prepare phosphorus ylide (6A) (6: R²=methyl group). A mixture of 2,3,4,4-tetramethyl-2-cyclopenten-1-one (5) (121 g, 98.0% GC) and tetrahydrofuran (480 g) was added and stirred overnight. After distilling off the solvent, the soluble part was extracted with hexane, and the hexane was distilled off to obtain a crude product. The crude product was purified by distillation under reduced pressure to obtain 4-(methoxymethylene)-1,1,2,3-tetramethyl-2-cyclopentene (4A) (116 g, 98.3% GC, yield 80%) as a mixture of geometric isomers showing geometrical isomerism regarding the exocyclic double bond (product ratio: E-form/Z-form=75/25) (boiling point: 73 to 75° C./1.0 kPa).

4-(Methoxymethylene)-1,1,2,3-tetramethyl-2-cyclopentene (4A)

Yellowish oil.

IR (D-ATR): ν=2954, 2928, 2862, 2830, 1705, 1668, 1461, 1376, 1358, 1328, 1251, 1223, 1135, 1090, 982, 802 cm⁻¹.

¹H-NMR (500 MHz, CDCl₃):

Major isomer (E-form): δ=0.96 (6H, s), 1.54 (3H, s), 1.58 (3H, d, J=0.8 Hz), 2.21 (2H, d, J=2.3 Hz), 3.53 (3H, s), 5.98 (1H, tq, J=2.3, 0.8 Hz) ppm.

Minor isomer (Z-form): δ=0.93 (6H, s), 1.54 (3H, s), 1.79 (3H, d, J=0.8 Hz), 2.13 (2H, d, J=1.5 Hz), 3.44 (3H, s), 5.76 (1H, tq, J=1.5, 0.8 Hz) ppm.

¹³C-NMR (126 MHz, CDCl₃): a mixture of E/Z geometric isomers, δ=9.40, 9.64, 10.08, 13.16, 26.62, 27.25, 41.28, 42.58, 43.81, 44.41, 59.08, 59.40, 122.26, 125.01, 127.56, 129.18, 136.64, 137.01, 143.19, 145.38 ppm.

GC-MS (EI, 70 eV): 29, 41, 53, 65, 77, 91, 105, 119, 136, 151, 166 (M+).

Example 2: Synthesis of 2,3,4,4-tetramethyl-1-cyclopentenecarbaldehyde (7)

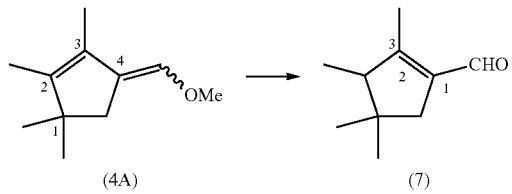

A mixture of 4-(methoxymethylene)-1,1,2,3-tetramethyl-2-cyclopentene (4A) (20.0 g, 98.3% GC) obtained according to Example 1, hexane (40 g), tetrahydrofuran (40 g) and 20% hydrochloric acid (65 g) was stirred under nitrogen atmosphere for 6 hours. The organic layer was separated and then subjected to work-up process, i.e., ordinary separation, washing, and concentration to obtain a crude product. The crude product was purified by distillation under reduced pressure to obtain 2,3,4,4-tetramethyl-1-cyclopentenecarbaldehyde (7) (11.7 g, 95.1% GC, yield 62%) (boiling point: 61° C./0.45 kPa).

2,3,4,4-Tetramethyl-1-cyclopentenecarbaldehyde (7)

Brownish oil.

IR (D-ATR): ν=2960, 2869, 2719, 1663, 1633, 1440, 1377, 1340, 1256, 1228, 1210 cm⁻¹.

¹H-NMR (500 MHz, CDCl₃): δ=1.03 (3H, s), 0.97 (3H, d, J=7.7 Hz), 8.72 (3H, s), 2.06 (3H, m), 2.25 (1H, m, *including d, J=15.6 Hz), 2.32 (1H, m, *including d, J=15.6 Hz), 2.35 (1H, m, *including q, J=7.7 Hz), 9.98 (1H, s) ppm.

¹³C-NMR (126 MHz, CDCl₃): δ=11.86, 12.88, 23.25, 28.65, 39.89, 43.28, 55.53, 136.41, 165.40, 188.70 ppm.

GC-MS (EI, 70 eV): 27, 41, 55, 67, 81, 95, 109, 123, 137, 152 (M+).

Example 3: Synthesis of 2,3,4,4-tetramethyl-2-cyclopentenecarbaldehyde dimethyl acetal (1A) (1: R¹=methyl group)

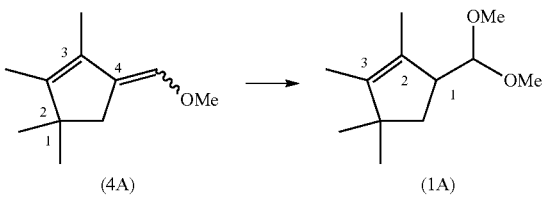

A mixture of 4-(methoxymethylene)-1,1,2,3-tetramethyl-2-cyclopentene (4A) (1.00 g, 98.3% GC) obtained according to Example 1, methanol (5.70 g), 20% hydrochloric acid (0.11 g) and hexane (5.0 g) was stirred under nitrogen atmosphere for 64 hours. The reaction mixture was diluted with hexane. The organic layer was separated and then subjected to work-up process, i.e., ordinary separation, washing, and concentration to obtain 2,3,4,4-tetramethyl-2-cyclopentenecarbaldehyde dimethyl acetal (1A) as a crude product (0.97 g, 59.9% GC, crude yield 50%).

2,3,4,4-Tetramethyl-2-cyclopentenecarbaldehyde dimethyl acetal (1A)

Brown oil.
$^1$H-NMR (500 MHz, CDCl$_3$): δ=0.93 (3H, s), 1.01 (3H, s), 1.50 (3H, m), 1.58 (1H, dd, J=13.0, 3.8 Hz), 1.62 (3H, m), 1.74 (1H, dd, J=13.0, 8.4 Hz), 2.78 (1H, m), 3.34 (3H, s), 3.38 (3H, s), 4.20 (1H, d, J=6.5 Hz) ppm.
GC-MS (EI, 70 eV): 31, 47, 65, 75, 91, 107, 123, 135, 151, 167, 181, 198 (M+).

Example 4: Synthesis of 2,3,4,4-tetramethyl-2-cyclopentenecarbaldehyde ethylene acetal (1B, 1: R$^1$—R$^1$=ethylene group)

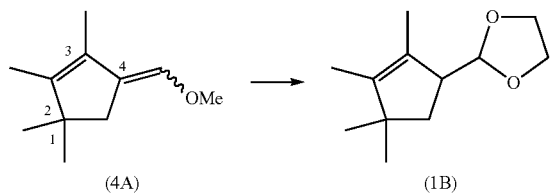

A mixture of 4-(methoxymethylene)-1,1,2,3-tetramethyl-2-cyclopentene (4A) (10.0 g, 98.3% GC) obtained according to Example 1, ethylene glycol (20.0 g), 20% hydrochloric acid (11.0 g), hexane (20 g) and tetrahydrofuran (20 g) was stirred under nitrogen atmosphere for 20 hours. The reaction mixture was diluted with hexane. The organic layer was separated and then subjected to work-up process, i.e., ordinary separation, washing, and concentration to obtain a crude product. The crude product was purified by distillation under reduced pressure to obtain 2,3,4,4-tetramethyl-2-cyclopentenecarbaldehyde ethylene acetal (1B) (7.38 g, 95.8% GC, yield 61%) (boiling point: 95-97° C./1.0 kPa).

2,3,4,4-Tetramethyl-2-cyclopentenecarbaldehyde ethylene acetal (1B)

Yellowish oil.
IR (D-ATR): ν=2953, 2864, 2748, 1665, 1444, 1396, 1377, 1359, 1322, 1208, 1160, 1135, 1107, 1059, 1036, 968, 944 cm$^{-1}$.
$^1$H-NMR (500 MHz, CDCl$_3$): δ=0.94 (3H, s), 1.02 (3H, s), 1.51 (3H, m), 1.57 (1H, dd, J=12.6, 6.9 Hz), 1.64 (3H, m), 1.75 (1H, dd, J=12.6, 8.4 Hz), 2.77 (1H, m), 3.81-4.03 (4H, m), 4.84 (1H, d, J=4.6 Hz) ppm.
$^{13}$C-NMR (126 MHz, CDCl$_3$): δ=9.54, 13.15, 26.84, 27.67, 39.48, 45.39, 50.11, 64.65, 65.17, 106.08, 127.91, 141.84 ppm.
GC-MS (EI, 70 eV): 29, 45, 55, 73, 91, 107, 123, 135, 151, 165, 181, 196 (M+).

Example 5: Synthesis of 2,3,4,4-tetramethyl-2-cyclopentenecarbaldehyde ethylene acetal (1B, 1: R$^1$—R$^1$=ethylene group)

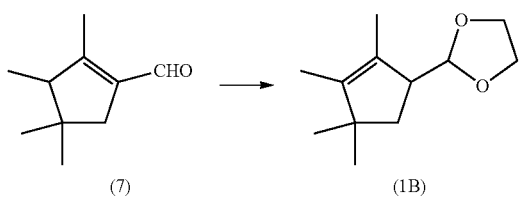

A mixture of 2,3,4,4-tetramethyl-1-cyclopentenecarbaldehyde (7) obtained according to Example 2 (0.50 g, 85.5% GC), ethylene glycol (5.20 g), 20% hydrochloric acid (0.51 g) and hexane (2.0 g) was stirred under nitrogen atmosphere for 6 hours. The reaction mixture was diluted with hexane. The organic layer was separated and then subjected to work-up process, i.e., ordinary separation, washing, and concentration to obtain 2,3,4,4-tetramethyl-2-cyclopentenecarbaldehyde ethylene acetal (1B) (0.48 g, 75.0% GC, yield 66%) as a crude product.

The various spectrum data of the 2,3,4,4-tetramethyl-2-cyclopentenecarbaldehyde ethylene acetal (1B) thus obtained were the same as the various spectrum data obtained in Example 4.

Example 6: Synthesis of 2,3,4,4-tetramethylcyclopentanecarbaldehyde dimethyl acetal (2A, 2: R$^1$=methyl group) and 2,3,4,4-tetramethylcyclopentanecarbaldehyde ethylene acetal (2B, 2: R$^1$—R$^1$=ethylene group)

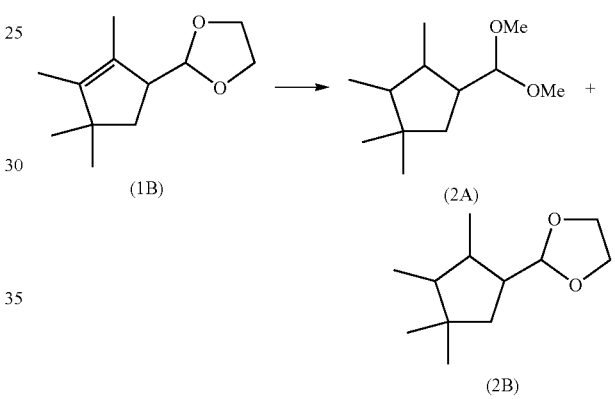

A mixture of 2,3,4,4-tetramethyl-2-cyclopentenecarbaldehyde ethylene acetal (1B) (1.00 g, 95.8% GC) obtained according to Example 4, methanol (15 g) and 5% palladium on carbon (0.23 g) were placed in an autoclave, purged with hydrogen gas, and stirred for 12 hours. The solid contents were filtered off, and after distilling off the solvent to obtain as a crude product, a mixture of 2,3,4,4-tetramethylcyclopentanecarbaldehyde dimethyl acetal (2A) and 2,3,4,4-tetramethylcyclopentanecarbaldehyde ethylene acetal (2B) was obtained as a brown oil (0.89 g).

2,3,4,4-Tetramethylcyclopentanecarbaldehyde dimethylacetal (2A)

Brown oil.
IR (D-ATR): ν=2954, 2872, 2829, 1455, 1376, 1190, 1139, 1123, 1106, 1059, 966 cm$^{-1}$.
$^1$H-NMR (500 MHz, CDCl$_3$): Major isomer, δ=1.52 (3H, d, J=7.3 Hz), 0.81 (3H, s), 0.94 (3H, s), 0.96 (3H, d, J=6.9 Hz), 1.24 (1H, dd, J=12.6, 9.6 Hz), 1.54-1.64 (2H, m), 1.90-2.01 (2H, m), 3.31 (3H, s), 3.35 (3H, s), 4.15 (1H, d, J=7.3 Hz) ppm.
$^{13}$C-NMR (126 MHz, CDCl$_3$): Major isomer, δ=10.17, 17.81, 23.33, 29.24, 38.37, 41.04, 43.12, 46.12, 47.45, 52.80, 54.03, 109.40 ppm.
GC-MS (EI, 70 eV): 29, 41, 55, 65, 75, 85, 97, 109, 121, 137, 153, 169, 181, 199.

2,3,4,4-Tetramethylcyclopentanecarbaldehyde ethylene acetal (2B)

Brownish oil.
IR (D-ATR): ν=2955, 2872, 1459, 1388, 1377, 1151, 1089, 1064, 1036, 962, 943 cm$^{-1}$.
$^1$H-NMR (500 MHz, CDCl$_3$): Major isomer, δ=0.77 (3H, d, J=7.3 Hz), 0.83 (3H, s), 0.95 (3H, s), 0.98 (3H, d, J=7.3 Hz), 1.31 (1H, dd, J=12.6, 9.9 Hz), 1.58-1.67 (2H, m), 1.86 (1H, m), 2.10 (1H, m), 3.80-3.88 (2H, m), 3.90-4.20 (2H, m), 4.76 (1H, d, J=5.4 Hz) ppm.
$^{13}$C-NMR (126 MHz, CDCl$_3$): Major isomer, δ=10.12, 17.69, 23.40, 29.21, 37.46, 41.22, 42.24, 46.21, 48.82, 64.76, 64.99, 107.87 ppm.
GC-MS (EI, 70 eV): 29, 45, 55, 73, 83, 97, 109, 121, 136, 153, 168, 183, 197.

Example 7: Synthesis of 2,3,4,4-tetramethylcyclopentanecarbaldehyde (3)

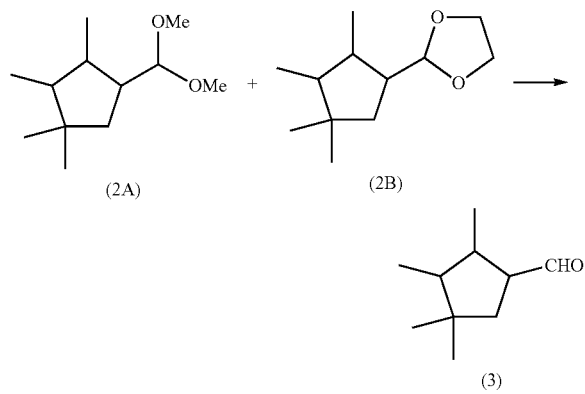

To the crude product obtained in Example 6 were added hexane (2.0 g), tetrahydrofuran (2.0 g) and 20% hydrochloric acid (2.7 g) and stirred under nitrogen atmosphere for 17 hours. The mixture was neutralized with sodium hydroxide, the aqueous layer was removed, and then, 20% hydrochloric acid (2.7 g) was added again and stirred under nitrogen atmosphere for 18 hours. The mixture was again neutralized with sodium hydroxide, the organic layer was separated and then subjected to work-up process, i.e., ordinary separation, washing, and concentration to obtain 2,3,4,4-tetramethylcyclopentanecarbaldehyde (3) (0.66 g, 80.0% GC) as a crude product.
The crude yield of 2,3,4,4-tetramethylcyclopentanecarbaldehyde (3) from 2,3,4,4-tetramethyl-2-cyclopentenecarbaldehyde ethylene acetal (1B) was 70%.
The diastereomer ratio of the (1R*,2R*,3S*)-form (3'') (relative configuration same as that of the sex pheromone of OMB) in 2,3,4,4-tetramethylcyclopentanecarbaldehyde (3) was determined to be 62.8% dr by GC analysis.

2,3,4,4-Tetramethylcyclopentanecarbaldehyde (3)

Yellowish oil.
IR (D-ATR): ν=2959, 2872, 2707, 1723, 1663, 1456, 1379 cm$^{-1}$.
GC-MS (EI, 70 eV): 29, 41, 55, 69, 83, 97, 98, 109, 123, 139, 154 (M+).

Comparative Synthetic Example: Synthesis of (2S*, 3S*)-4-(methoxymethylene)-1,1,2,3-tetramethylcyclopentane (103) from 2R*,3S*)-2,3,4,4-tetramethyl-2-cyclopenten-1-one (5')

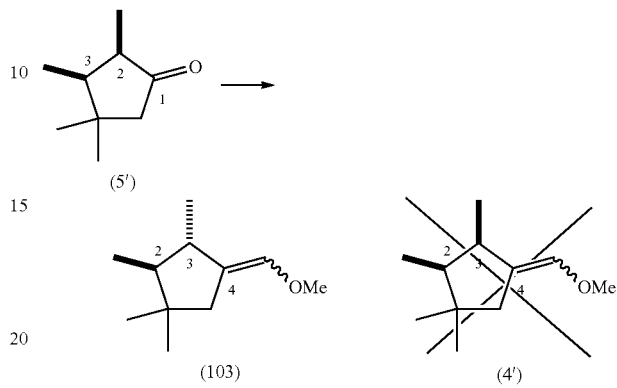

To a mixture of (methoxymethyl)triphenylphosphonium chloride (4.46 g) and tetrahydrofuran (10 g) was added potassium tert-butoxide (1.35 g) under nitrogen atmosphere with ice-cooling and stirring. The mixture was stirred for 20 minutes, and then a mixture of (2R*,3S*)-2,3,4,4-tetramethyl-2-cyclopenten-1-one (5') (1.50 g, 85.6% GC) and toluene (10 g) was added. The temperature of the mixture was raised to room temperature, and the mixture was stirred for 10 hours. Water and diethyl ether were added, and the organic layer was separated and then subjected to work-up process, i.e., separation, washing, filtration, drying, and concentration, to obtain 4-(methoxymethylene)-1,1,2,3-tetramethylcyclopentane as a crude product (1.41 g, 75.8% GC, crude yield 63.5%).
The product thus prepared was the (2S*,3S*)-form (103) formed by epimerization of the methyl group at position 2 of the substrate (2R*,3S*)-2,3,4,4-tetramethyl-2-cyclopenten-1-one(5') followed by a Wittig reaction. The (2S*,3R*)-form (4') having the relative configuration same as that of the sex pheromone of OMB was not confirmed to be present by GC-MS analysis.
The confirmation of the relative configuration was carried out by converting the reaction product into (2,3,4,4-tetramethylcyclopentyl)methyl acetate following the processes described in Non-Patent Literature 1, and comparing the observed date with the physical property data described in Non-Patent Literature 3.

INDUSTRIAL APPLICABILITY

The results indicate that the preparation processes of the present invention make it possible to prepare safely, efficiently, selectively, and industrially a (1R*,2R*,3S*)-2,3,4,4-tetramethylcyclopentanecarbaldehyde, which is an important preparation intermediate of (1R*,2R*,3S*)-(2,3,4,4-tetramethylcyclopentyl)methyl acetate which is, as the sex pheromone of an important agricultural pest, OMB, promising for applications such as forecasting outbreaks of the pest and controlling the pest, as compared with known methods and are highly valuable for industrial applications.

The invention claimed is:
1. A process for preparing an acetal compound of the following general formula (2), the process comprising:

subjecting an acetal compound of the following general formula (1) to a hydrogenation reaction to form the acetal compound (2),

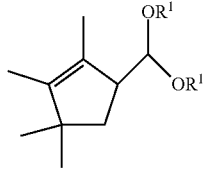

(1)

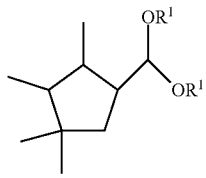

(2)

wherein in the general formulae (1) and (2), $R^1$s represent, independent of each other, a monovalent hydrocarbon group having 1 to 6 carbon atoms, or two $R^1$s may form together a divalent hydrocarbon group, $R^1$—$R^1$, having 2 to 12 carbon atoms.

2. A process for preparing 2,3,4,4-tetramethylcyclopentanecarbaldehyde of the following formula (3):

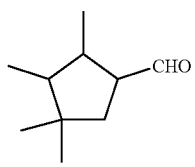

(3)

the process comprising:
the process according to claim 1 for preparing the acetal compound (2), and subjecting the acetal compound (2) to a hydrolysis reaction to form 2,3,4,4-tetramethylcyclopentanecarbaldehyde (3).

3. The process according to claim 2 for preparing 2,3,4,4-tetramethylcyclopentanecarbaldehyde (3),
wherein among four diastereomers of 2,3,4,4-tetramethylcyclopentanecarbaldehyde (3), the diastereomeric ratio, dr, of the (1R*,2R*,3S*)-2,3,4,4-tetramethylcyclopentanecarbaldehyde of the following formula (3") is 50% or more,

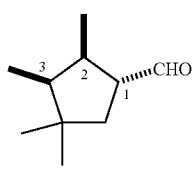

(3")

wherein in the formula (3"), the bold bond and the hashed bond represent a relative configuration.

4. The process according to claim 1 for preparing 2,3,1,1 (3) the acetal compound (2), the process further comprising:
subjecting a vinylether compound of the following general formula (4) and an alcohol compound of the following formulae (XA) or (XB) to an acetalization reaction in the presence of an acid to form the acetal compound (1)

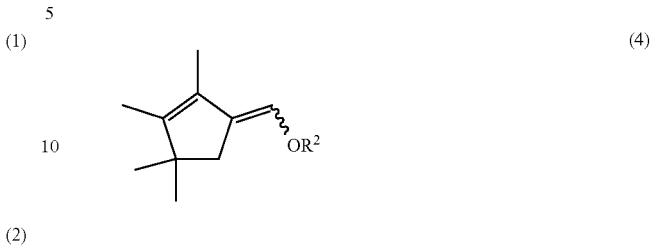

(4)

wherein in the general formula (4), $R^2$ represents a monovalent hydrocarbon group having 1 to 15 carbon atoms, and the wavy line represents the E-form, the Z-form, or a mixture thereof;
$R^1$OH (XA), wherein $R^1$ is as defined above; and
HO$R^1$—$R^1$OH (XB), wherein $R^1$s represent, independent of each other, as defined above.

5. The process according to claim 4 for preparing 2,3,1,1 (3) the acetal compound (2), the process further comprising
subjecting 2,3,4,4-tetramethyl-2-cyclopentenone of the following formula (5) to a Wittig reaction with a phosphorus ylide compound of the following formula (6) to form the vinylether compound (4)

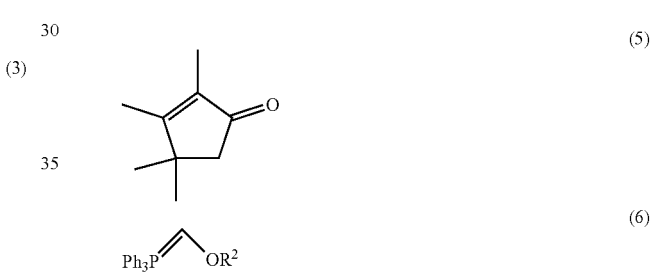

(5)

(6)

wherein in the general formula (6), $R^2$ represents a monovalent hydrocarbon group having 1 to 15 carbon atoms, and Ph represents a phenyl group.

6. The process according to claim 1 for preparing the acetal compound (2), the process further comprising
subjecting the 2,3,4,4-tetramethyl-1-cyclopentenecarbaldehyde of the following formula (7) to an acetalization reaction with the alcohol compound of the following formulae (XA) or (XB) in the presence of an acid to form the acetal compound (1)

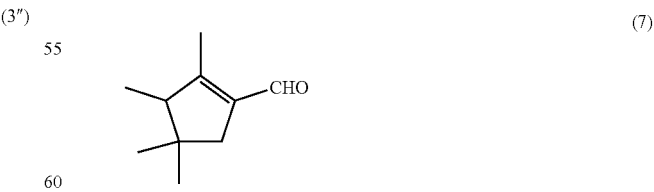

(7)

$R^1$OH (XA), wherein $R^1$ is as defined above;
HO$R^1$—$R^1$OH (XB), wherein $R^1$s represent, independent of each other, as defined above.

7. The process according to claim 6 for preparing the acetal compound (2), the process further comprising subjecting 2,3,4,4-tetramethyl-2-cyclopentenone of the following formula (5) to a Wittig reaction with a phosphorus ylide compound of the following formula (6) to form the vinylether compound (4); and subjecting the vinylether compound (4) to a hydrolysis reaction to form 2,3,4,4-tetramethyl-1-cyclopentenecarbaldehyde (7)

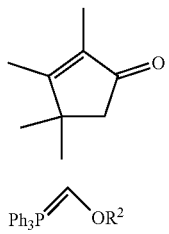

(5)

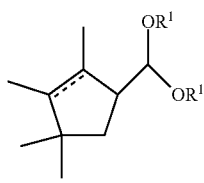

(6)

wherein in the general formula (6), R² represents a monovalent hydrocarbon group having 1 to 15 carbon atoms, and Ph represents a phenyl group.

8. An acetal compound of the following general formula (α):

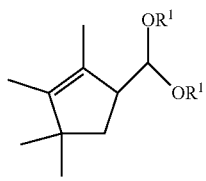

(α)

wherein R¹s represent, independent of each other, a monovalent hydrocarbon group having 1 to 6 carbon atoms, or two R¹s may form together a divalent hydrocarbon group, R¹—R¹, having 2 to 12 carbon atoms, and the bonds represented by solid and dotted lines represent single or double bonds.

9. An acetal compound of the following general formula (1), wherein the bond represented by the solid and dotted lines in the general formula (α) is a double bond

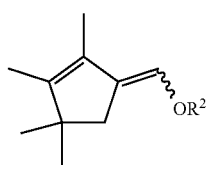

(1)

wherein R¹s represent, independent of each other, as defined above.

10. An acetal compound of the following general formula (2), wherein the bond represented by the solid and dotted lines in the general formula (α) according to claim 8 is a single bond

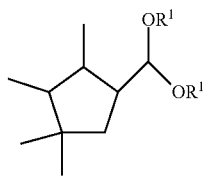

(2)

wherein R¹s represent, independent of each other, are as defined above.

11. The process according to claim 2 for preparing 2,3,4,4-tetramethylcyclopentanecarbaldehyde (3), the process further comprising:

subjecting a vinylether compound of the following general formula (4) and an alcohol compound of the following formulae (XA) or (XB) to an acetalization reaction in the presence of an acid to form the acetal compound (1)

(4)

wherein in the general formula (4), R² represents a monovalent hydrocarbon group having 1 to 15 carbon atoms, and the wavy line represents the E-form, the Z-form, or a mixture thereof;

R¹OH (XA), wherein R¹ is as defined above; and
HOR¹—R¹OH (XB), wherein R¹s represent, independent of each other, as defined above.

12. The process according to claim 11 for preparing 2,3,4,4-tetramethylcyclopentanecarbaldehyde (3), the process further comprising subjecting 2,3,4,4-tetramethyl-2-cyclopentenone of the following formula (5) to a Wittig reaction with a phosphorus ylide compound of the following formula (6) to form the vinylether compound (4)

(5)

(6)

wherein in the general formula (6), R² represents a monovalent hydrocarbon group having 1 to 15 carbon atoms, and Ph represents a phenyl group.

13. The process according to claim 2 for preparing 2,3,4,4-tetramethylcyclopentanecarbaldehyde (3), the process further comprising subjecting the 2,3,4,4-tetramethyl-1-cyclopentenecarbaldehyde of the following formula (7) to an acetalization reaction with the alcohol compound of the following formulae (XA) or (XB) in the presence of an acid to form the acetal compound (1)

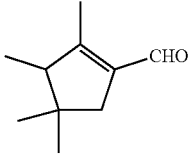
(7)

R$^1$OH (XA), wherein R$^1$ is as defined above;
HOR$^1$—R$^1$OH (XB), wherein R$^1$s represent, independent of each other, as defined above.

14. The process according to claim 13 for preparing 2,3,4,4-tetramethylcyclopentanecarbaldehyde (3), the process further comprising
subjecting 2,3,4,4-tetramethyl-2-cyclopentenone of the following formula (5) to a Wittig reaction with a phosphorus ylide compound of the following formula (6) to form the vinylether compound (4); and
subjecting the vinylether compound (4) to a hydrolysis reaction to form 2,3,4,4-tetramethyl-1-cyclopentenecarbaldehyde (7)

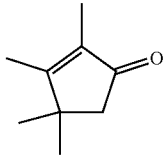
(5)

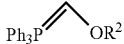
(6)

wherein in the general formula (6), R$^2$ represents a monovalent hydrocarbon group having 1 to 15 carbon atoms, and Ph represents a phenyl group.

* * * * *

UNITED STATES PATENT AND TRADEMARK OFFICE
CERTIFICATE OF CORRECTION

PATENT NO. : 11,661,390 B2
APPLICATION NO. : 17/861629
DATED : May 30, 2023
INVENTOR(S) : Watanabe et al.

Page 1 of 2

It is certified that error appears in the above-identified patent and that said Letters Patent is hereby corrected as shown below:

In the Specification

Column 4, Line 63: Delete "les" and insert --$R^1$s--

Column 6, Line 16: Delete "les" and insert --$R^1$s--

Column 7, Line 49: Delete "les" and insert --$R^1$s--

Column 9, Line 39: Delete "le" and insert --$R^2$--

Column 11, Line 1: Delete "les" and insert --$R^1$s--

Column 11, Line 4: Delete "les" and insert --$R^1$s--

Column 11, Line 66: Delete "les" and insert --$R^1$s--

Column 14, Line 18: Delete "les" and insert --$R^1$s--

Column 14, Line 38: Delete "les" and insert --$R^1$s--

Column 15, Lines 1-16: Please delete the formula and replace with the following:

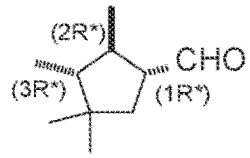 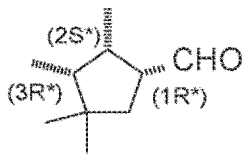 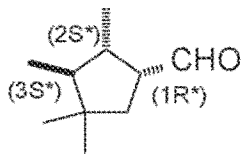 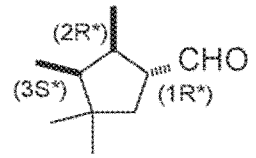

Signed and Sealed this
Fifth Day of September, 2023

Katherine Kelly Vidal
*Director of the United States Patent and Trademark Office*

CERTIFICATE OF CORRECTION (continued)
U.S. Pat. No. 11,661,390 B2

Column 24, Line 23: Delete "Step C1,2,3,4,4-" and insert --Step C1, 2,3,4,4- --

Column 24, Line 64: Delete "les" and insert --$R^1$s--

Column 24, Line 66: Delete "les" and insert --$R^1$s--

Column 27, Line 54: Delete "6=0.96" and insert --δ=0.96--

Column 27, Line 57: Delete "6=0.93" and insert --δ=0.93--

Column 27, Line 62: Delete "6=9.40" and insert --δ=9.40--

In the Claims

Column 33, Lines 64-65, Claim 4: Delete "preparing 2,3,1,1 (3) the acetal" and insert --preparing the acetal--

Column 34, Lines 22-23, Claim 5: Delete "preparing 2,3,1,1 (3) the acetal" and insert --preparing the acetal--